United States Patent [19]
Ghorashi et al.

[11] Patent Number: 6,112,131
[45] Date of Patent: Aug. 29, 2000

[54] GIN PROCESS CONTROL

[75] Inventors: Hossein M. Ghorashi, Knoxville; Gordon F. Williams, Norris; Mark A. Overbay, Knoxville, all of Tenn.

[73] Assignee: Zellweger Uster, Inc., N.C.

[21] Appl. No.: 09/020,220

[22] Filed: Feb. 6, 1998

[51] Int. Cl.[7] ........................... G01N 15/08; G01N 21/59
[52] U.S. Cl. ........................... 700/142; 700/143; 73/160; 73/866
[58] Field of Search ...................... 700/142, 143, 700/36, 84; 73/73, 160, 862.14

[56] References Cited

U.S. PATENT DOCUMENTS

| | | | |
|---|---|---|---|
| 4,766,647 | 8/1988 | Ackermann, Jr. et al. | 19/0.22 |
| 4,828,577 | 5/1989 | Markham, Jr. et al. | 44/589 |
| 5,005,452 | 4/1991 | Wood, III | 82/132 |
| 5,178,007 | 1/1993 | Ghorashi et al. | 73/159 |
| 5,537,868 | 7/1996 | Shofner et al. | 73/160 |
| 5,805,452 | 9/1998 | Anthony et al. | 700/142 |
| 5,892,142 | 4/1999 | Ghorashi et al. | 73/38 |
| 5,943,907 | 8/1999 | Ghorashi et al. | 73/160 |

OTHER PUBLICATIONS

Loptex, Optalyser OP 300 brochure, date unknown.
Schlichter, *Trutzschler nep tester NT: a new visual method to analyze neps and interfering particles*, Textile Praxis International, pp. 28–29, Sep., 1991.
Trutzschler, Nep Tester NT brochure, date unknown.
Lintronics, Fiber Contamination Tester brochure, date unknown.
Lieberman and Zhao, *Categorizing Cotton Trash Shapes Using Video Imagery*, Beltwide Cotton Conference, pp. 854–858, 1991.
Lieberman, Bragg, and Brennan, *Determining Gravimetric Bark Content in Cotton with Machine Vision*, Textile Res. J., pp. 94–104, Feb. 1998.
Zellweger Uster, Uster LVI brochure, date unknown.
Zellweger Uster, Uster Micronaire 775 brochure, date unknown.
Zellweger Uster, Uster HVI 900 brochure, date unknown.
Peyer, texLAB brochure, date unknown.
Peyer, FL–100 manual (2 pages only), date unknown.
Benardin, Delfosse, *Measurement of fiber lengths distribution on raw wool*, Melliand International, pp. 70–74, Feb., 1996.
Motion Control, breaker drawings (2), Oct., 1994.

*Primary Examiner*—William Grant
*Assistant Examiner*—Kidest Bahta
*Attorney, Agent, or Firm*—Luedeka, Neely & Graham, PC

[57] ABSTRACT

A gin process control system including sensing stations for sensing the physical properties of cotton as it progresses through a gin. A moisture sensor determines, over a wide range of values, the amount of moisture in the cotton. A quality monitor determines the color of the cotton, color distribution, and the amount and type of trash or other impurities which may be entrained in the cotton. A micronaire unit determines both micronaire and cotton maturity. A fiber length tester provides information on the length distribution, breaking strength, and elongation of the cotton fibers. Cotton samples are gathered from the gin flow stream and presented to the sensing stations in a variety of manual, semi-automated, and automated fashions. In a fully automated unit, the sensing stations are connected directly to the gin. The sensing stations are also in communication with the gin process control system, which uses the data from the sensing stations to automatically control the operation of the gin. Alternately, the sensing stations are assembled into a stand-alone unit. In a semi-automatic version of the stand-alone unit, samples are manually gathered and presented to the unit in cassettes for automated subsampling and testing by the sensing stations. In this semi-automatic version, the sensing stations may be in a configuration identical to that of the fully automatic, on-line unit. In a manual version of the stand-alone unit, the samples are manually gathered and manually placed into contact with the various sensing stations. The information reported by the stand-alone units can be used to manually control the operation of the gin.

19 Claims, 29 Drawing Sheets

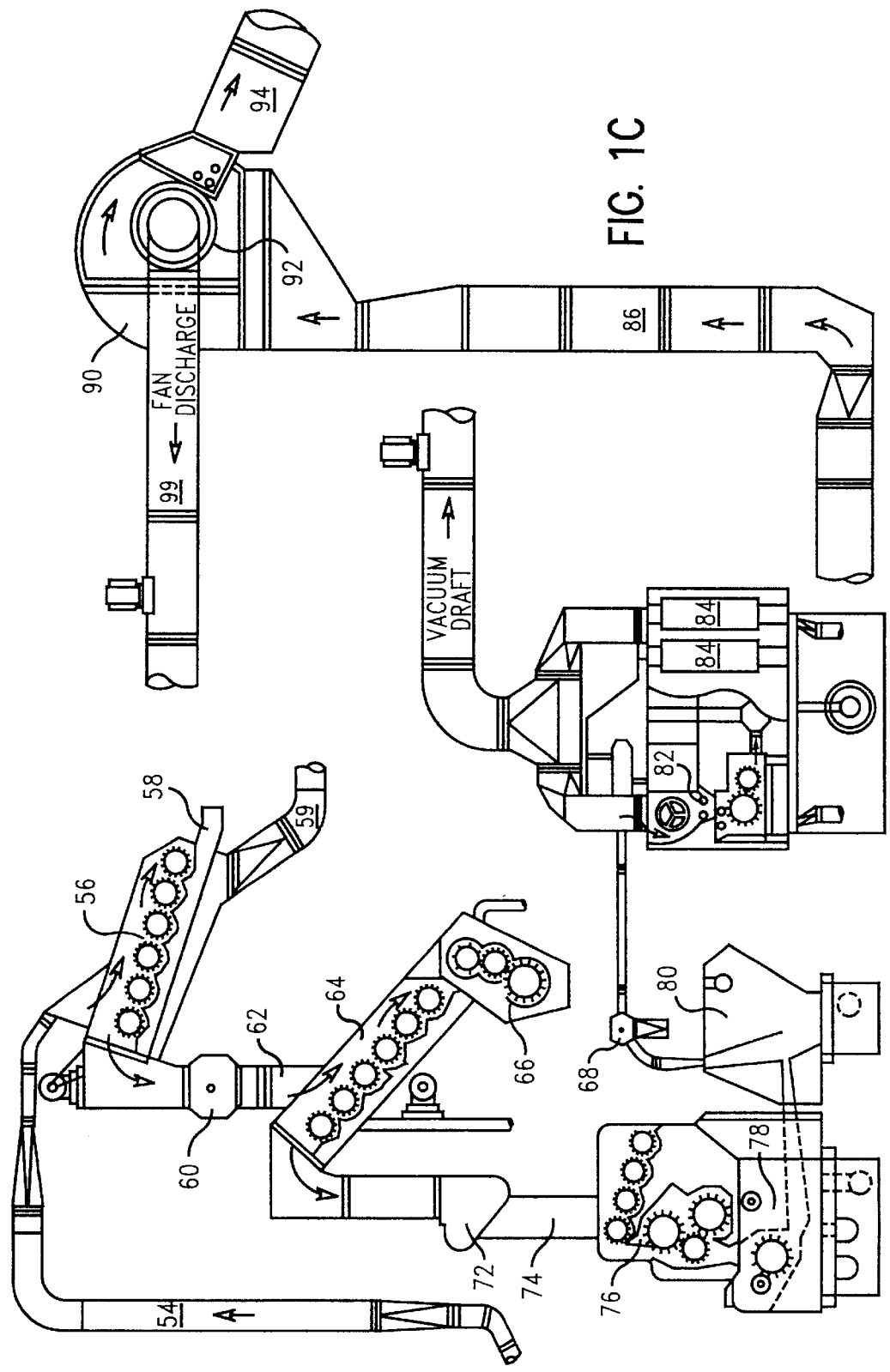

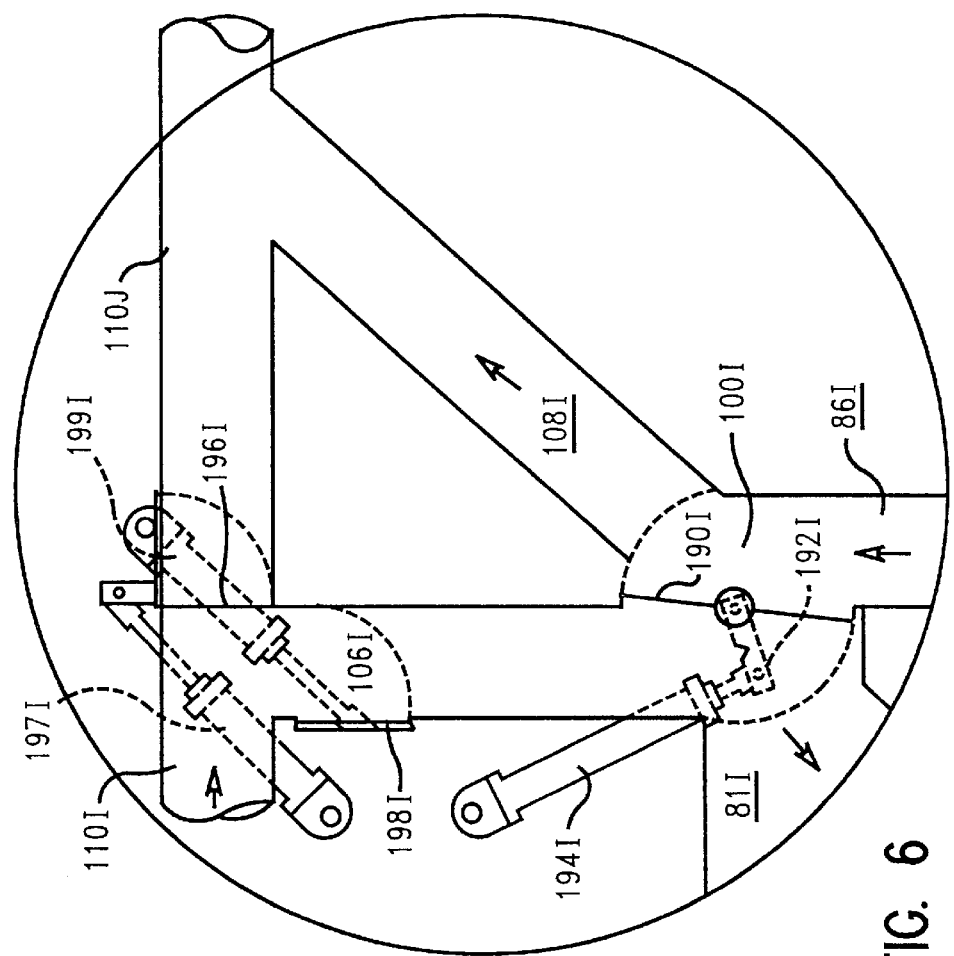
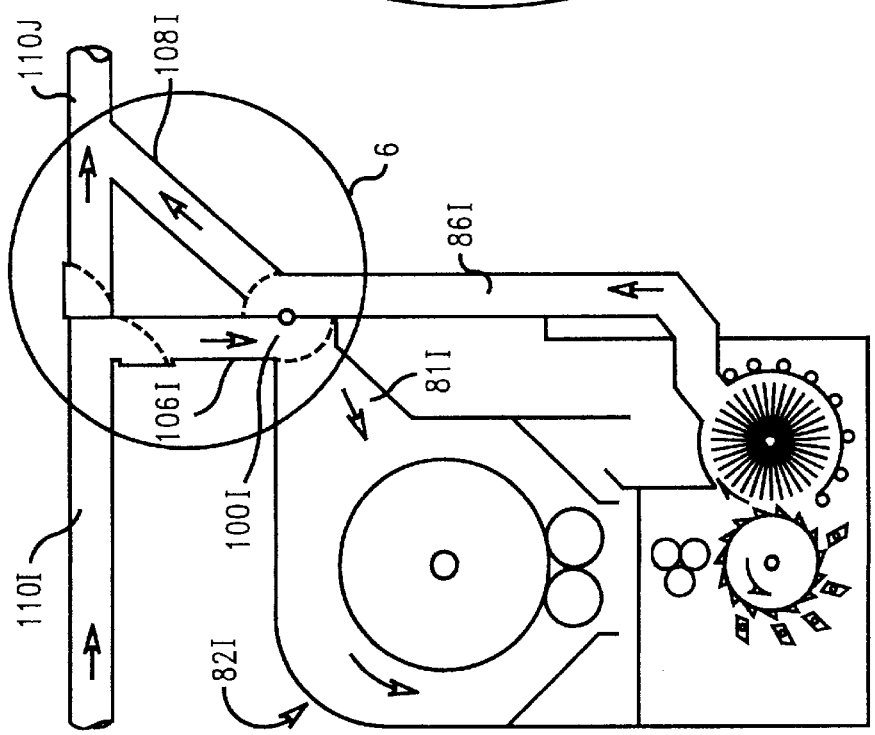
FIG. 6
FIG. 5

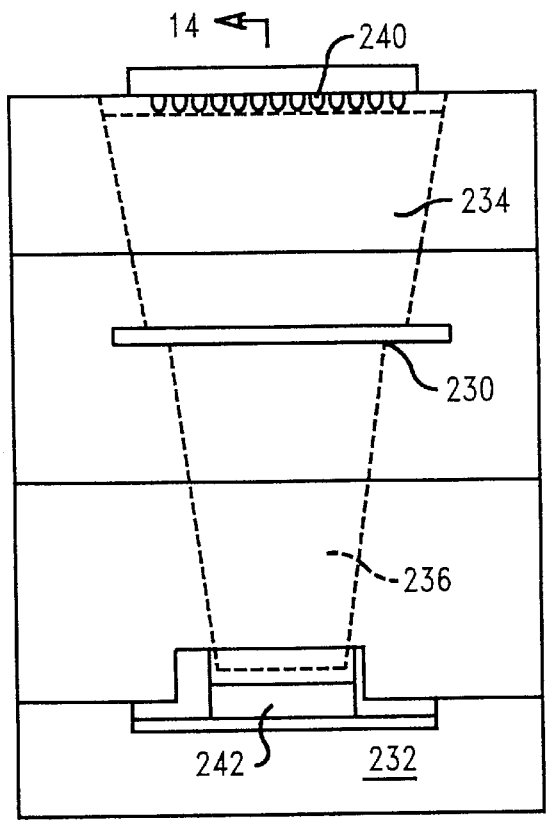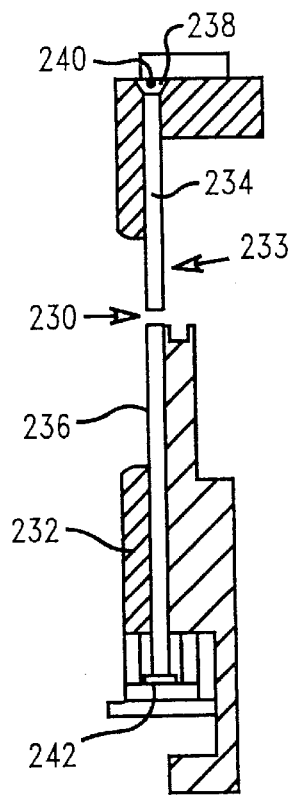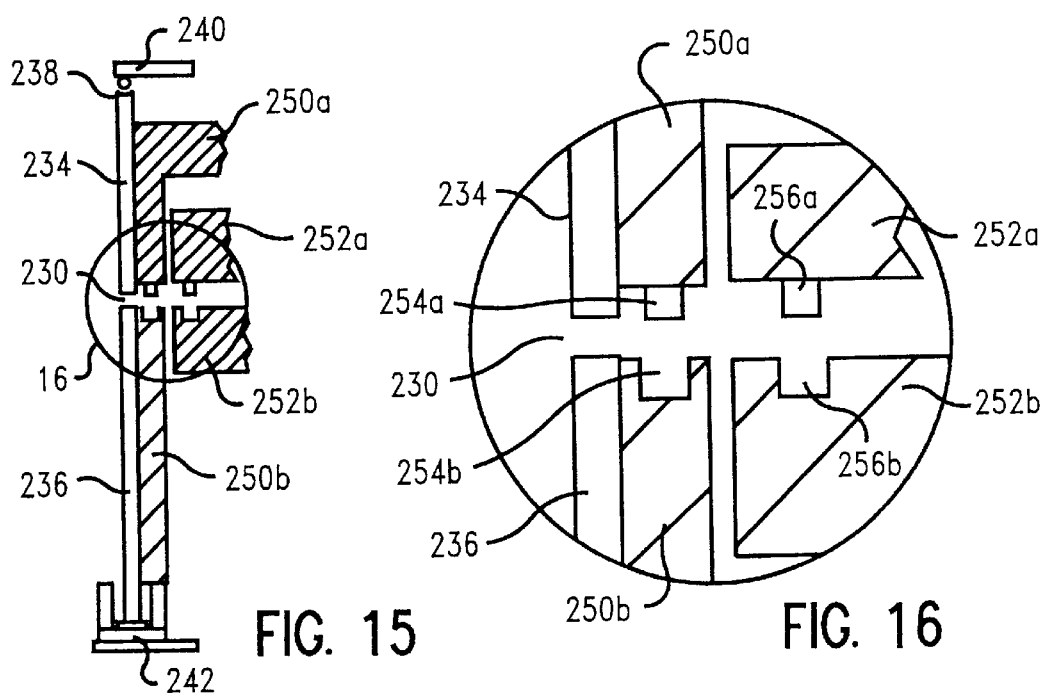
FIG. 13  FIG. 14  FIG. 15  FIG. 16

GIN PROCESS CONTROL

BACKGROUND OF THE INVENTION

The present invention generally relates to a method and apparatus for processing fibrous materials such as cotton. More particularly, the present invention relates to a cotton gin processing method and apparatus for optimizing the quality of cotton.

The term "cotton" may be used in reference to either "seed cotton" or "lint." Seed cotton is the raw, natural flower of the cotton plant having the plant seed in intimate presence with the fiber of the flower. Lint is the flower fiber in isolation from the seed.

Cotton ginning includes drying and trash removal from the seed cotton, separation of the plant seed from the lint, additional trash removal from the lint, lint consolidation and bale packaging. Depending on the mechanical capacities of the process equipment, a cotton gin may process as much as 150,000 pounds of seed cotton per hour into 12,000 pounds per hour of lint that is packaged into 500 pound bales. As implied, a cotton ginning system consists of several different types of processing machines or devices. Each machine is designed to influence one or more physical properties of the lint product.

Lint quality after ginning is a function of its initial, natural quality as well as the type and degree of cleaning, drying or moisturizing it receives during the gin process. Fiber color, length, strength and density are natural attributes of quality. The presence of moisture and trash, however, are externally imposed quality characteristics susceptible to modification by mechanical influences. Research has established that the apparent strength of cotton fibers is directly proportional to fiber moisture content and is therefore greater at higher moisture levels. Consequently, as fiber moisture content is lowered, as by drying, the apparent strength is reduced and the frequency of fiber breakage during ginning is increased.

Being a hygroscopic material, the natural moisture content of cotton varies in relation to the relative humidity of the surrounding air. Cotton harvested during periods of high humidity may arrive at gins with a moisture content as high as 12 percent or more whereas cotton harvested during periods of low humidity may contain fiber moisture of 4 percent or less. For these reasons, gins seeking to gin lint at a predetermined moisture content must be prepared to add as well as remove moisture from the cotton being processed. Nevertheless, most cotton in the United States is processed in a standardized sequence without regard to actual quantities of trash or moisture present in an immediate process batch. Consequently, some cotton may be over dried or processed through more cleaners than necessary for the level of trash originally present in the cotton. Such unnecessary or even harmful processing can result in decreased fiber quality and increased cost and/or processing time.

Since much of the American cotton crop is harvested during low-humidity periods and often arrives at the gin with fiber moisture from 4 to 5 percent, the average fiber length of such cotton may be improved by adding moisture before fiber-seed separation and lint cleaning by reducing the number of fibers that break in the gin stands and lint cleaners. However, restoration of moisture to ginned lint will not improve fiber length. On the other hand, cotton with fiber moisture of 9 percent or more may neither gin smoothly nor process properly through the lint cleaners. Thus, the recommended fiber moisture level of 6.5 to 8 percent has a gin production aspect as well as a product quality aspect.

Removal of trash is primarily associated with the economics of market grade and price. However, there exists a point of diminishing returns where the benefits of further trash removal are offset by fiber and cottonseed damage and excessive loss of weight. Most modern gins contain cleaning equipment to handle the most severe trash condition that is expected in their service areas. Actual use of that equipment preferably should be based upon the incoming trash content of the cotton, and cleaner cottons should not be processed through every cleaning machine in the gin just because it is available. Trash removal should be restricted to that which is necessary to produce the grade determined by the color of the cotton. Further cleaning reduces the weight without increasing the value of the bale.

One way to optimize the cotton processing sequence is to control the temperature of equipment such as driers and to bypass certain machines, such as seed cotton cleaners and lint cleaners that may not be necessary for the particular cotton being processed. Traditionally, physical properties of the cotton such as trash content, moisture content, color, fiber length, length variation, fiber strength, fiber elongation and fiber thickness were not monitored as the gin process progressed. Consequently, no system or method existed to determine a process sequence that would optimize the lint product quality, grade or value. Since there was no method for determining the optimum quality sequence, there were no means or apparatuses for carrying out an optimum quality sequence.

Changing the number of cleaners used in a conventional cotton ginning system requires downtime for the system as well as labor costs for manually changing the valve configurations. It has been estimated that at least five minutes are required to change the valves on a single gin stand lint cleaner device, for those gin systems that are equipped with flow sequence change valves. A gin typically has three or more sets of lint cleaners in series or parallel processing lines but not all are equipped with bypass valves.

To bypass a machine such as a lint cleaner in a conventional ginning system, the flow of cotton is stopped through the gin stand that immediately precedes the lint cleaner. If equipped, the valves in the material flow conduits to the machine that is to be bypassed are then closed, usually manually. The bypassed machine is then stopped. To put the bypassed machine back online, the process must be reversed. In order to bypass a machine such as a seed cotton cleaner or drier, all of the preceding machines must be stopped which consequently stops the flow of cotton throughout the entire gin system for a period of several minutes while the seed cotton cleaner valves are manually changed.

More recently, the United States Department Of Agriculture and others have sponsored the development of online sensors for measuring color, moisture and trash values. Such developments are partially represented by U.S. Pat. No. 5,058,444 to W. S. Anthony et al, U.S. Pat. No. 5,087,120 to W. S. Anthony, and U.S. Pat. No. 5,639,955, also to W. S. Anthony. As relevant to the present invention, the entirety of these prior art patent disclosures are incorporated herein by reference.

Pending U.S. patent application Ser. No. 08/691,069, also incorporated entirely herein by reference, describes a cotton gin system having online sensors for the physical properties of color and moisture. Additionally, application Ser. No. 08/691,069 teaches an online measurement of the relative trash content in the system flow stream. Data corresponding to these measurements is transmitted to a central processing unit (CPU). The CPU is a central control computer having a computer program logic that receives and processes the online sensor data to generate a gin decisional matrix from which flow sequence decisions are made that optimize the economic value of the flow stream. With a specific flow sequence concluded, appropriate operating signals are issued to powered flow controllers such as motor operated valves in the seed cotton or lint transport conduits.

Although pending application Ser. No. 08/691,069 represents a significant stride toward online quality development, the variable data base contributed to the program logic still is only color, moisture and trash. Fiber length, fiber length variation, fiber strength, the elongation capacity of the fiber and the fiber perimeter and wall thickness related property of micronaire are not considered by the prior art program logic.

There is, therefore, need for an automatic gin control system that considers fiber strength, fiber length, fiber length variations, elongation capacity of the fiber and micronaire cotton properties along with color, moisture and trash in development of an optimum quality processing sequence. Accordingly, it is an object of the present invention to provide a gin control system having online sensors for measuring fiber strength, fiber length, length variation, elongation capacity and micronaire as well as color, moisture and trash.

It is also an object of the present invention to provide a substantially unitized instrument assembly that may be positioned at many locations along the material flow path of a gin system.

A further object of the present invention is an apparatus that extracts a physical sample from an active gin processing stream without substantially interrupting the cotton flow stream continuity therein for an automatic manipulation of that physical sample to determine the average length of the fiber in transit, the variations in the fiber length, the elongation value of the fiber and the breaking strength of the fiber sample.

Also an object of the invention is to provide several new instruments for the measurement of micronaire.

Another object of the invention is to provide a method and apparatus for making a micronaire determination that avoids the necessity for weighing the sample.

A still further object of the invention is to provide a modified method and apparatus for determining the maturity of a cotton sample.

Still another object of the present invention is to provide a method and apparatus for obtaining a micronaire property measure from a live flow stream without manual invasion or substantial interruption of the flow stream.

A further object of the present invention is to provide a substantially unitized instrument assembly as a stand-alone piece of equipment, which is adapted to testing cotton fibers that are already removed from a source, such as a cotton gin, and manually presented as samples to the stand-alone instrument.

Yet another object of the present invention is to provide a substantially unitized instrument assembly as a stand-alone piece of equipment, which is adapted to testing cotton fibers that are already removed from a source, such as a cotton gin, and which can acquire and prepare the sample to be tested without manual assistance.

SUMMARY OF THE INVENTION

In a cotton gin having a plurality of treatment units and ducting for transporting a flow of air entrained cotton, flow control devices such as remotely controlled motor valves are positioned in the ducting for selectively including or excluding particular treatment units. The duct flow control status of each flow control device is ordered by a gin control computer that is programmed to select a gin process sequence based upon data from online cotton property measurements. The cotton property tests made are for fiber strength, fiber length, fiber length variation and length elongation as well as for moisture, color contamination, micronaire and maturity. As desired, the control program may be written to bias the lint product quality, the lint grade, the lint value or other such control objective. Pivotal to the integrity of the program sequence directed by the computer is the accuracy and consistency of cotton property data transmitted to the computer.

The present invention provides for online cotton flow stream samples to be isolated within the material transport ducting by paddle type samplers that temporarily collect a sample quantity of the duct flow stream and press it against a transparent window wall in the conduit. Reflectance or spectrographic optical sensors on the external side of the transparent window wall respond to light values reflected from the sample mass pressed against the internal side of the window wall. Such reflected light values are detected by the optical sensor and used to determine the color and trash content of the sample.

Moisture content of the flow stream sample that is captured by the online paddle is measured by a sensor having an electrical resistance grid. This resistance grid may be imbedded in the duct wall in a preferred embodiment or, alternatively, imbedded in the paddle. As the paddle presses the accumulated sample against the wall, the sample mass is intimately pressed against the resistance grid to induce a low but measurable leakage current through the sample having a current value proportional to the moisture content of the sample.

The same or an independent paddle sample accumulator may also be used to press an in-conduit flow stream sample against a screen or aperture grid in the duct wall. On the exterior side of the duct wall but isolated from external atmosphere, is a closed circuit belt conveyor that carries a plurality of combs. As the belt is driven around the closed circuit, the combs are passed against the exterior surface of the aperture grid to rake a sampling of fibers from packed patches of fiber protruding through the apertures of the grid under the compression pressure of the paddle. With the fiber samples attached as a beard to the comb tines, the samples are firmly secured by a pinch bar. As the conveyor belt advances, the comb and attached fibers arrives at a combing station where the sample of fibers secured by the belt comb are combed. A second movement increment advances the belt comb and fiber sample held thereby to a brushing station that completes the parallelization of the beard fibers and removes loose fibers and foreign entities. A third station in the belt circuit first scans the sample beard optically for a composite of the length profile thereby providing length distribution data (fibergram) from which mean length, short fiber length and length uniformity are derived.

Next, the extended sample beard is gripped between vise jaws secured to a load cell and measured tensile force is applied between the gripping comb and the vise jaws until the beard breaks. This measured tensile force relates to the fiber tensile strength and fiber elongation.

Following the length measure/breaking station, the beard residual remaining in the gripping comb is advanced to a doffing station where the pinch bar is removed from engagement with the comb tines to release the fiber particles into a vacuum removal system. For each station in the conveyor belt circuit, a sampling comb is provided to thereby produce an incrementally continuous flow of electrically transmitted data proportional to the measured fiber length, fiber length variation, fiber tensile strength and fiber elongation.

Micronaire is an empirical measure of cotton fineness distinctive to the textile industry based upon fiber perimeter and fiber wall thickness. The micronaire value is determined by measuring a flow of air passing through the sample. The total fiber surface determines the flow resistance. By the traditional micronaire procedure, a known air flow rate is forced through a predetermined axial length of a fiber packed cylinder having a predetermined volume. The pressure loss over that axial length is measured and the measured value normalized by the weight of fiber within the packed volume. Implicitly, the micronaire property test requires several discrete steps including: isolation of a test quantity of fiber; placing that test quantity in a cylindrical test cell; applying the test flow stream to the test cell and through the test quantity of fiber; measuring the pressure drop of air flow across the axial length; and, weighing the test quantity of fiber.

In the present invention, an online micronaire is accomplished by a ducting shunt from the main material carrier duct. A fiber suspending flow stream is induced into the shunt to deposit fiber against the face of a porous or perforated piston that constitutes a test cell end wall. As the shunt flow stream continues, fiber accumulates against the porous piston face and along the cylinder bore in front of the piston face. A pair of axially spaced pressure tap zones along the cylinder bore are pressure differentially monitored as an indicator of the quantity of fiber accumulated within the cylinder bore. At a predetermined accumulation point, the shunt is closed to the main fiber transport duct and a second perforated piston enters the fiber accumulation volume to compress the accumulation between the opposite piston faces. The volume to which the accumulation is compressed is a known constant or known by measured determination. In the latter case, the face of the compression piston engages the accumulated fiber mass to a predetermined pressure or force value. The position of the piston face at that compression force due is then measured for a corresponding volume determination. So disposed, a known air flow rate is established through the accumulated fiber within the fixed volume between the opposing piston faces and the corresponding pressure differential measured. Following measure of the pressure differential across the known volume, the first porous piston is retracted to open an axial extension of the accumulation cylinder to a tangential exit conduit. An abrupt pressure pulse of air against the second piston end of the accumulated fiber sample mobilizes the sample from the test position into the exit conduit. Transport along the exit conduit deposits the test sample onto a scale platform by which the weight of the test sample is taken, for those methods which require a weight measurement to be taken. Signals proportional to the test pressure differential and the test sample weight (either measured or empirically determined) are transmitted to the CPU for micronaire determination.

BRIEF DESCRIPTION OF THE DRAWINGS

Additional objects and advantages of the invention will emerge from the following description of the preferred embodiments that references the drawings wherein:

FIG. 1C is a continuation of the FIG. 1B flow schematic including two additional seed cotton cleaners, a gin stand and two lint cleaners;

FIG. 5 is a schematic representation of a first type of duct flow control apparatus applicable to the present invention;

FIG. 6 is an enlarged detail of the FIG. 5 apparatus within the perimeter of the FIG. 5 focal circle 6;

FIG. 13 is an end view of the fiber length and strength property testing apparatus of the present invention;

FIG. 14 is across-section of the optical scanning elements for the FIG. 13 apparatus as viewed along cutting plane 14—14;

FIG. 15 is a cross-section of the fiber strength measuring elements for the FIG. 13 apparatus as viewed along cutting plane 14—14;

FIG. 16 is an enlarged detail of elements within the perimeter of FIG. 15 focal circle 16;

DESCRIPTION OF THE PREFERRED EMBODIMENTS

Process Flow System

Figure 1A:
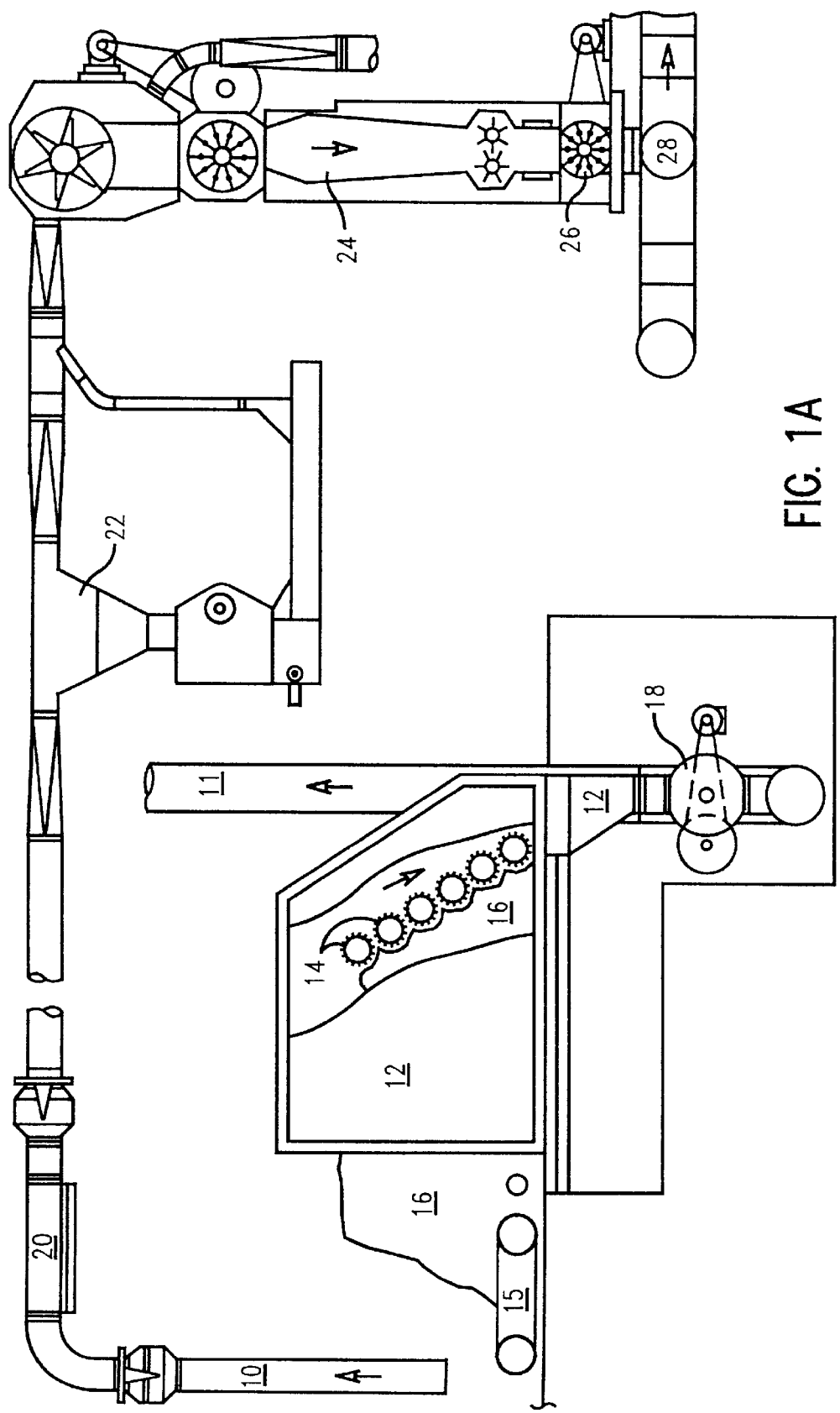
FIG. 1A is a cotton gin flow schematic of the seed cotton feed control section.

Referring to FIGS. 1A–1D of the drawings wherein like reference characters designate like or similar machines or elements throughout the several figures of the drawings, a typical cotton ginning system is represented. Generally, cotton is transported sequentially through and between each processing station in an air flow stream confined within air duct conduits. Air flow velocity within a telescope pickup system for fluidized transport of seed cotton may be 5,500 to 6,000 ft/min. Air flow velocity for fluidized transport of lint cotton is about 2,000 to 3,500 ft/min.

Cotton may be delivered from the growing fields to the gin in loose bulk or in consolidated modules. Loose bulk deliveries are drawn by a vacuum draft into the supply transport ducting 20 through a telescoping pickup pipe 10. Rail car or highway van size consolidated modules 16, on the other hand, may be placed upon a feed conveyor 15 for controlled feed into a dispersing head 12 and against a battery of rotatively driven, spiked rollers 14. The spiked rollers shred the module along a leading face to free the individual seed cotton bolls which are drawn into a feed hopper 17 by the draft of a fan 18. A suction pickup pipe 11 passes the seed cotton flow into the supply transport duct 20.

Next along the seed cotton process line may be a green boll and rock separator 22. Machine-stripped cotton frequently contains many green, immature bolls that cause ginning problems such as clogging of the gin saw teeth, failure of the seed roll to turn, accumulation of sticky material on the inner surface of the roll boxes and on the saws and moving surfaces of the gin stands and other machines. Many of the green bolls are broken open by the cleaning machines and their contents add moisture to the adjacent cotton. Also, moisture is transferred from other wet plant materials to dry cotton, causing ginning problems. Cotton and cotton seed, especially when immature, contain small amounts of substances that become sticky when wet and that can be responsible for the gumming of gin machinery. Additionally, spindle pickers and machine strippers will pick up rocks, clods, metal scrap, roots and other heavy objects in the field. These contaminants must be removed before the cotton reaches the gin's processing machines to cause machine damage, flow obstructions or fires.

One of several types of green boll and rock separators employ centrifugal force arising from an abrupt change in the duct flow direction. Open, mature bolls tend to follow the air flow path more closely than the heavier, dense materials. Such dense materials tend to continue along a straight line of travel tangentially from the abrupt, air flow directional change. This tangential path leads into a contaminant collection chamber and expulsion from the system.

Seed cotton feed rate into the supply transport ducting 20 and through the green boll and rock separator is controlled by a surge bin 24. Sensors in the surge bin turn the suction off and on by opening and closing a valve in the supply transport duct 20.

Figure 1B:
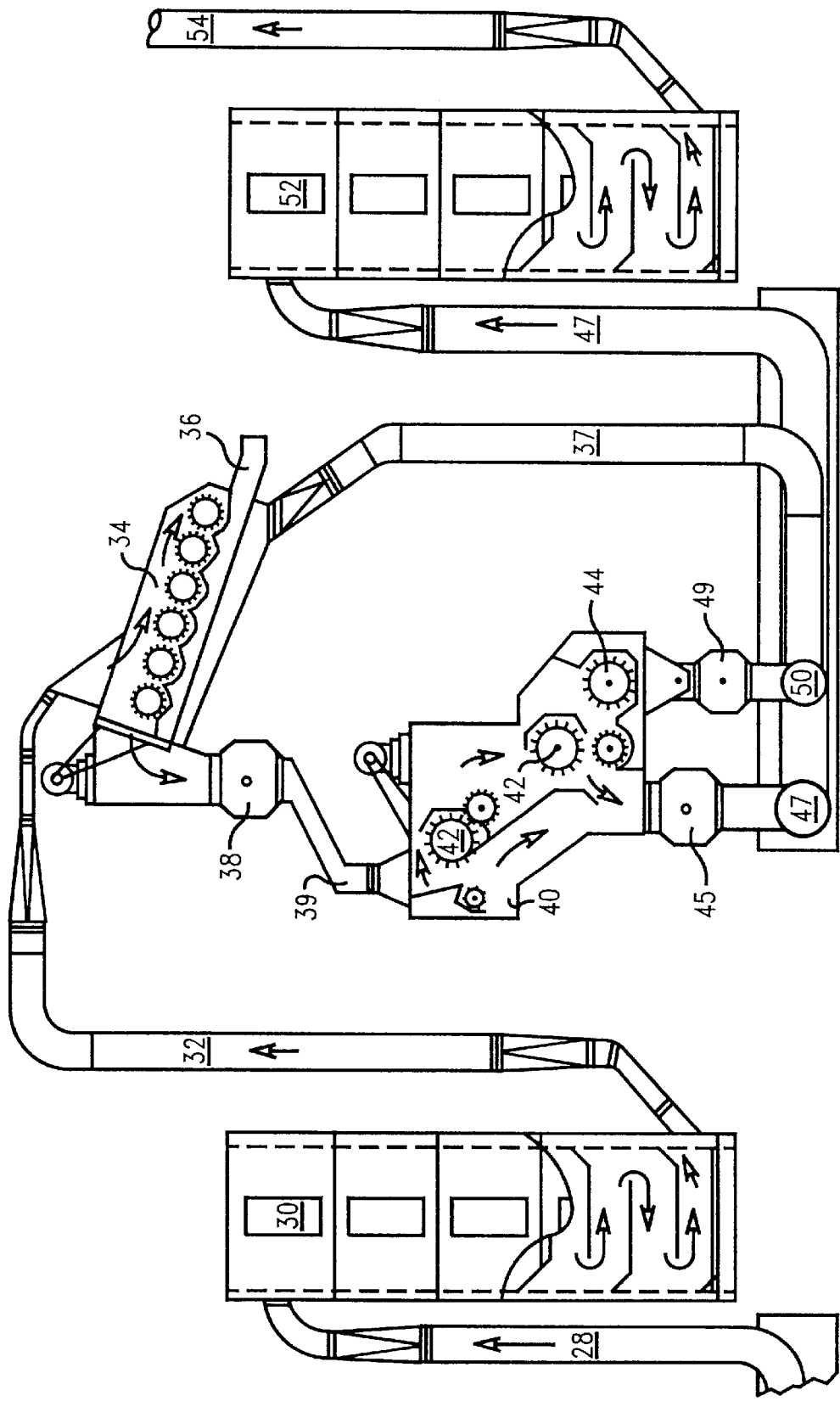
FIG. 1B is a continuation of the FIG. 1A flow schematic including two seed cotton dryers and an intermediate stick and green leaf cleaning machine.
Figure 1D:
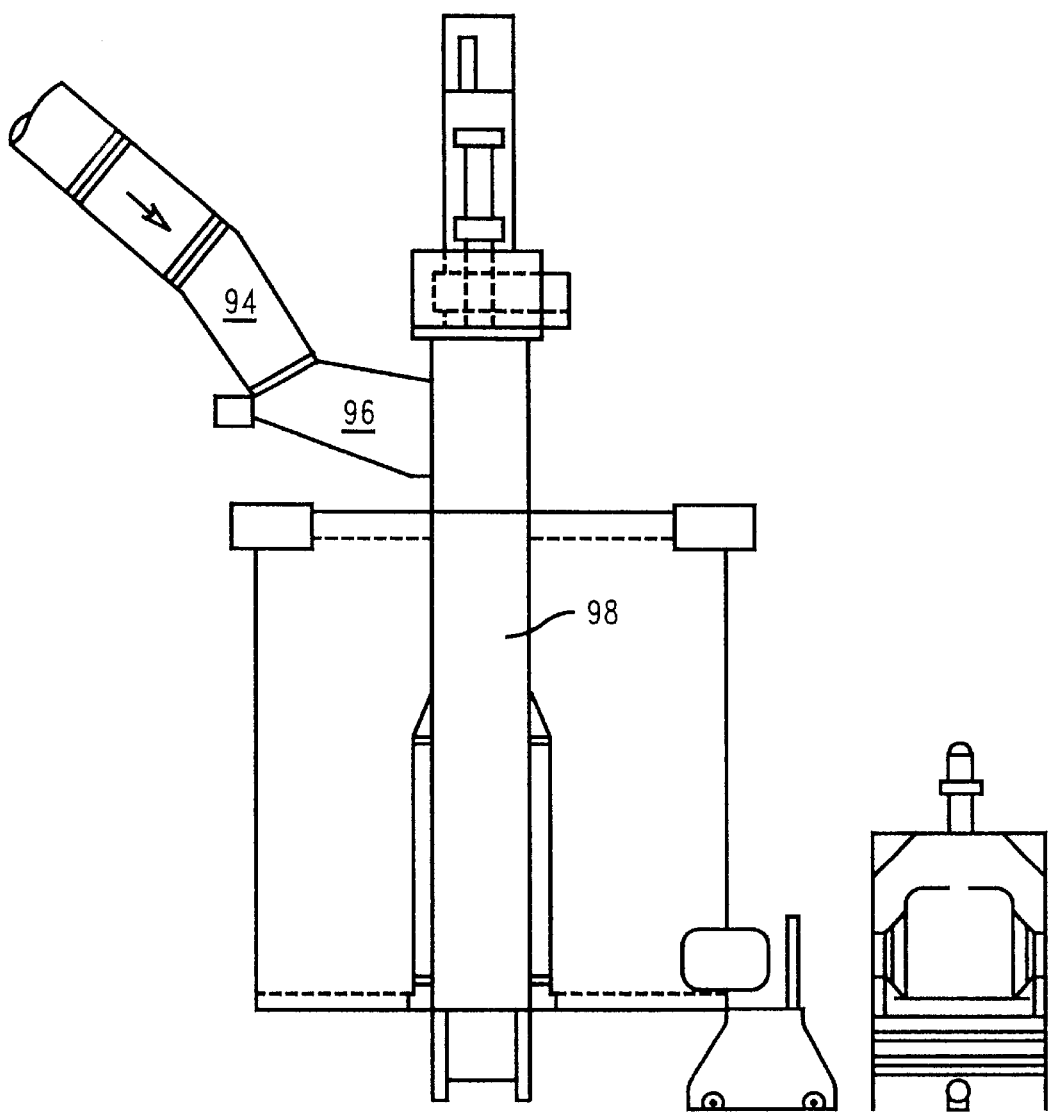
FIG. 1D is a continuation of the FIG. 1C flow schematic of the lint baling station.

Past the surge bin vacuum dropper 26, the seed cotton flow enters a first dryer supply duct 28 which delivers the flow into a first drying tower 30, depicted in FIG. 1B. As the cotton flow enters the dryer, the flow is mixed with dry, heated air. First dryer discharge ducting 32 transports the fluidized seed cotton flow into a first six cylinder inclined flow cleaner 34 for removal of finely divided particles and for opening and preparing the seed cotton for the drying and extraction processes to follow. The cylinder cleaner 34 consists of a series of spiked cylinders, usually 4 to 7 in number, that agitate and convey the seed cotton across cleaning surfaces containing small openings or slots. The cleaning surfaces may be either concave screen or grid rod sections, or serrated discs. Foreign matter that is dislodged from the seed cotton by the action of the cylinders falls through the screen, grid rod or disc openings for collection and disposal through a trash duct 36. The processed flow stream is delivered to a vacuum dropper 38 and a transport duct section 39. Vacuum supply duct 37 maintains a pressure differential across the screen or grid boundary to bias the transfer of dislodged trash through the screen or grid into a trash collection bin.

The next seed cotton cleaning apparatus in a typical gin system may be a stick and green leaf machine 40 which includes two saw cylinders 42 and a reclaimed saw cylinder 44. Cleaned cotton continues through the vacuum dropper 45 into the second tower dryer supply duct 47. Trash and reject material separated by the stick and green leaf machine 40 passes a vacuum dropper 49 into a trash discharge duct 50.

Proper drying of damp cotton benefits the producer, ginner, and spinner in several ways. Dryers condition the seed cotton for smoother and more continuous operation of the gin plant by removing excess moisture and by fluffing the partly opened locks. For these reasons, sufficient drying capacity is provided to a well conceived gin facility to accommodate a "worst case" circumstance. However, excessive drying can cause quality problems. Over drying damage comes from two sources: getting the fibers too hot and excess fiber breakage. Processing cotton through mechanical cleaners, gin stands, and saw type lint cleaners while it is too dry and brittle induces fiber breakage thereby reducing the average fiber length. If the second tower dryer 52 is used, the material flow stream emerges through the second dryer discharge duct 54 for delivery to a second cylinder inclined cleaner 56, depicted in FIG. 1C. As the spiked cylinders pass the seed cotton over and under the cylinder alignment, vacuum drawn from the screen draft duct 59 pulls air through the cotton flow and the screen or grid. Dry contaminants on the cotton, loosened by the spiked cylinder mauling, are drawn through the screen or grid onto the trash collection bin for discharge through the trash duct 58. Accept cotton is discharged at the top of the cylinder incline into a vacuum dropper 60 and into an intermediate transport duct 62 for delivery to a third inclined cylinder cleaning machine 64.

This third cleaner, however, also includes a lint reclaiming saw cylinder 66 that discharges loose lint captured from the flow stream into a vacuum dropper 68. Lint passed through the vacuum dropper 68 may be routed alternatively into an air lint cleaner 80 or into a controlled-batt saw lint cleaner 82 in the post-gin stand flow stream. Main flow from the third inclined cylinder cleaner 64 is next routed into a screw conveyor/distributor 72 for distribution along a gin supply chute 74 into the gin stand feeder assembly 76. The primary function of the feeder assembly is to feed the seed cotton flow to the gin stand uniformly and at controllable rates.

The gin stand 78 is the heart of the gin plant. This mechanism separates the cotton seed from the cotton lint.

The capacity of the system and the quality and potential spinning performance of the lint produced depends on the operating condition of the gin. Gin stand operational quality may affect every commonly measured fiber property except fiber strength and micronaire. Usually positioned immediately after the gin stand is an air lint cleaner 80. Loose lint from the gin stand is blown through a duct within the chamber of the air lint cleaner. Air and cotton moving through the duct change direction abruptly as they pass across a narrow trash-ejection slot. Foreign matter that is heavier than the cotton fibers and not too tightly held by the fibers is ejected through the slot by inertial force.

Fluidized lint flow from the gin stand 78 and the air lint cleaner 80 is formed by saw lint cleaners 82 into a bat on a condenser screen drum. The bat is then fed through one or more sets of compression rollers, passed between a very closely fitted feed roller and feed plate or bar, and fed onto a saw-cylinder. Each set of compression rollers rotates slightly faster than the preceding series and produces some thinning of the batt. The feed roller and plate grip the batt so that a combing action takes place as the saw teeth seize the fibers. The teeth of the saw cylinder convey the fibers to the discharge point. While on the saw cylinder, the fibers are cleaned by a combination of centrifugal force, scrubbing action between saw cylinder and grid bars, and gravity assisted by an air current. The fibers may be doffed from the saw teeth by a revolving brush, air blast, or air suction. Depending on the number and capacity of contributing gin stands, a plurality of saw lint cleaners 82 may be cooperatively connected in a parallel battery 84 or in a serial sequence.

Bale packaging is the final step in processing cotton at the gin. The packaging system consists of a battery condenser 90, a lint slide 94, a lint feeder 96 and bale press machinery 98, depicted in FIG. 1D. Clean lint flow from the lint cleaner battery 84 is discharged into a condenser delivery duct 86. Condensers 90 have a slow-turning, screened or perforated metal-covered drum 92 on which the ginned lint forms a batt. The batt is discharged between doffing rollers to the lint slide 94. Conveying air supplied by a vane-axial or high volume centrifugal fan passes through the screen on the drum and is discharged out one end of the drum through an air duct 99. The lint slide is a sheet metal trough connecting the battery condenser 90 to the lint feeder 96 of the baling station 98. The lint slide is installed at an angle of 33° to 45° from the horizontal to ensure sliding movement of the lint batt without rolling.

Material Transport System

Figure 2:
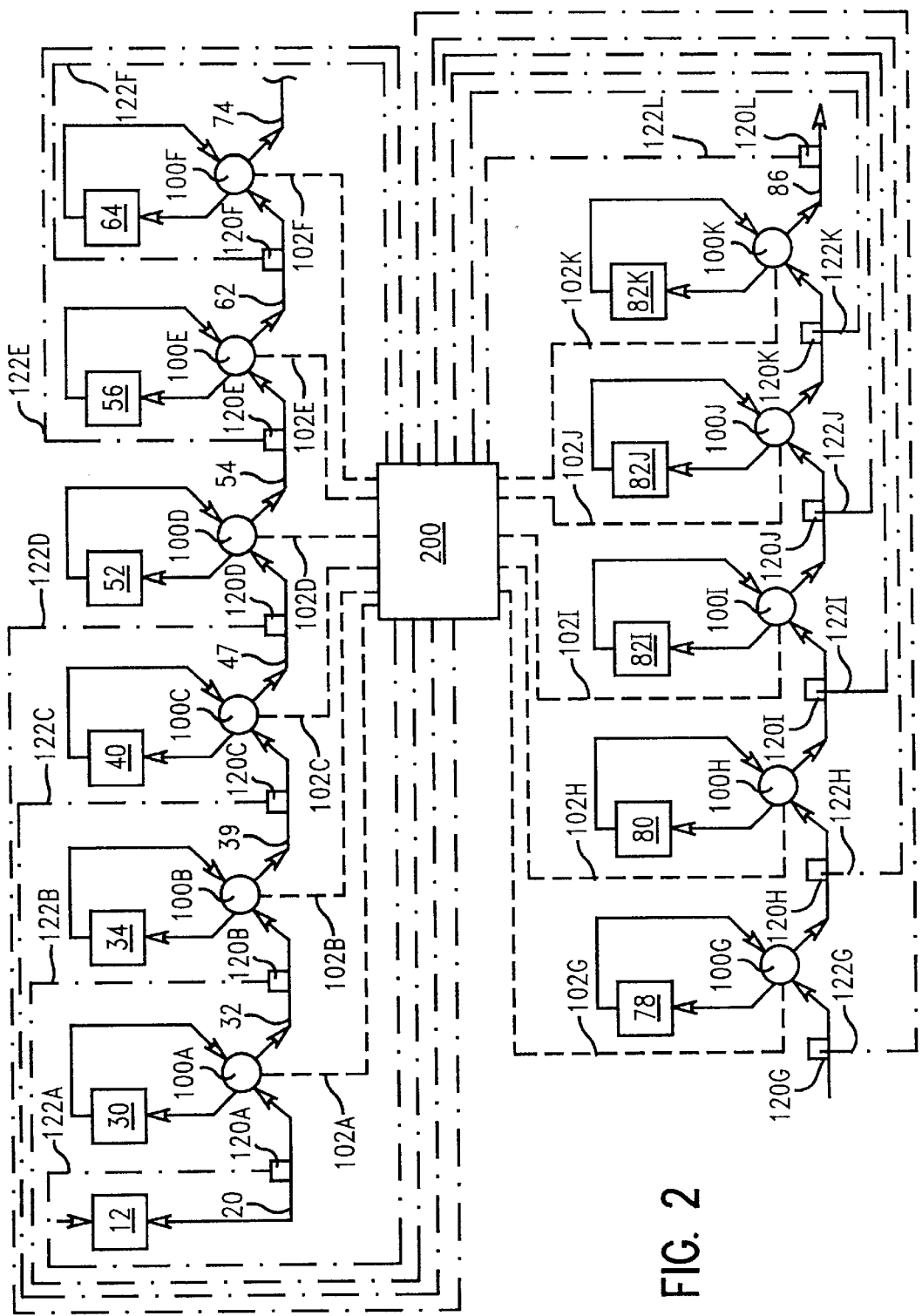
FIG. 2 is a flow control schematic for a cotton gin pursuant to the present invention.

Referring to FIG. 2, the cardinal process machines described above with respect to FIGS. 1A–1D are shown by block representation. Lines connecting the machine blocks represent cotton transport ducting. Arrowheads in the duct lines represent the predominant flow direction in the respective duct. Simplistically, each process machine is shown with a cotton flow line in and a flow line out. In reality, the flow system is much more complex with parallel and shunt flows energized by fan draft systems and checked by powered vacuum droppers. For the present purposes, however, it is sufficient to represent flow control into and from a respective process machine by a single, 4-way valve symbol 100. It should be understood that the actual flow control device or devices employed for each machine may be more than one apparatus, the flow routing may differ from that of a 4-way valve or flow controllers may be completely omitted between particular process machines. Understanding the foregoing caveat, the 4-way valves 100A–100K provide two flow control routes by which the primary material flow stream may be alternatively routed into the associated process machine or past the machine as desired or commanded by control signals from a central computer 200. If primary material flow is routed into the process machine, discharge flow from the process machine is shown to be routed back to the 4-way valve for controlled return to the primary flow stream. If a process machine is bypassed, the flow discharge ducting from the machine is either blocked or connected to the inlet flow duct for closed loop isolation.

Each of the valves 100A–K is operated by a motor of a form appropriate to the specific machine application. Such motors may be energized by electricity, compressed air or hydraulics. Here, the term "motor" is used expansively to include both rotating and linear drive machinery. Hence, motor control includes all of those actions and devices essential to convert a particular command signal from the computer 200 into the desired duct flow control objective. Such technology is well known to those of ordinary skill in the art and will not be further described herein except with respect to some mechanisms shown by FIGS. 5–8 that are particularly suitable for duct flow control. Accordingly, the FIG. 2 lines 102A–K connecting the duct flow control devices 100A–K with the control computer 200 represent the respective duct control signal transmission routes.

Associated with the cotton transfer ducting between each processing machine are sensor data transmitters 120A–L connected by signal carrier conduits 122A–L. In practice, each of the data transmitters 120 of FIG. 2 may represent a multiplicity of data transmitters, each transmitter of the multiplicity serving a particular cotton property measured by a corresponding test instrument.

Cotton Sample Extraction

Figure 3:
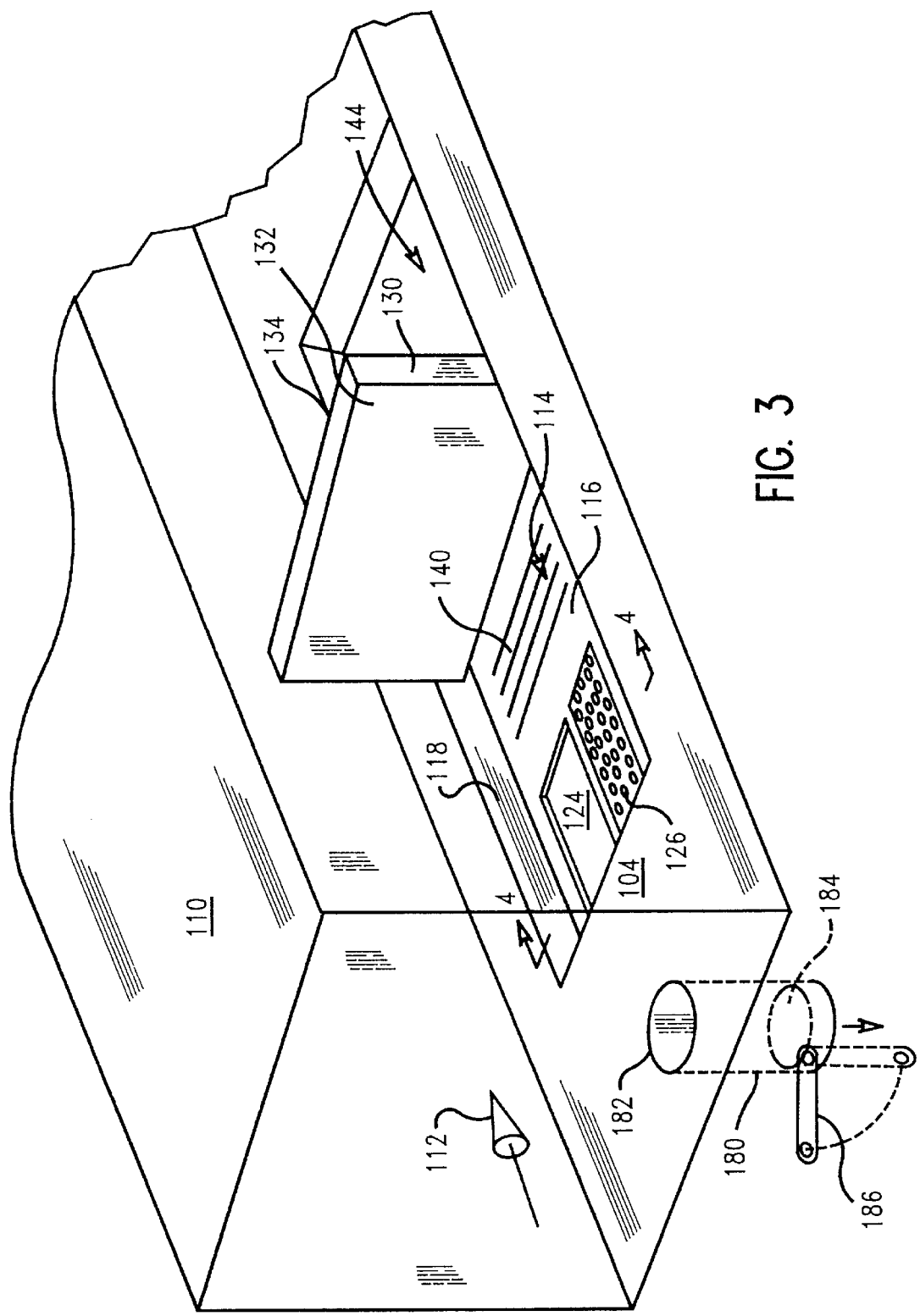
FIG. 3 is a representative in-situ cotton flow stream sampling apparatus applicable to the practice of the present invention.
Figure 4:
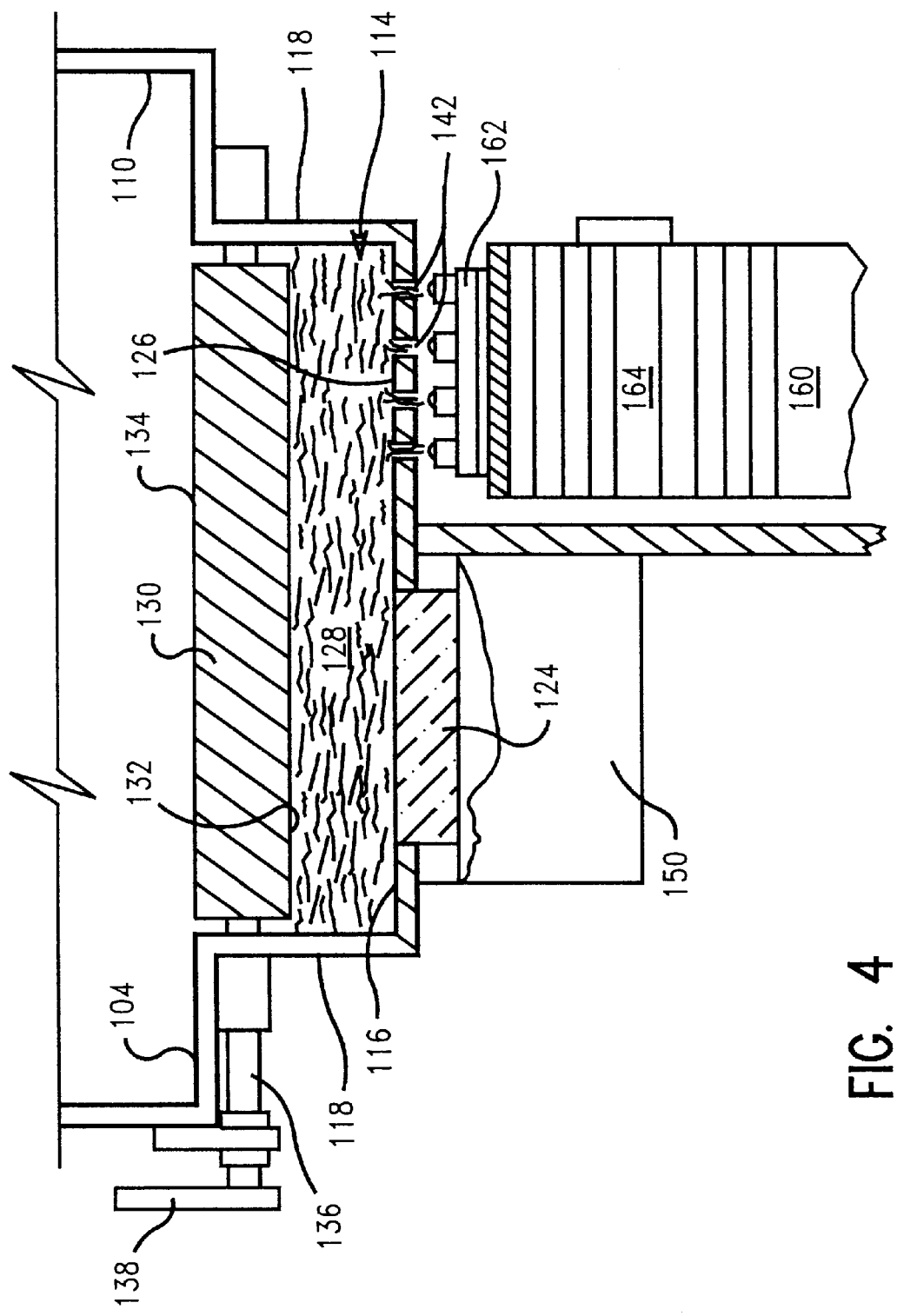
FIG. 4 is a cross-section of the FIG. 3 and FIG. 9 apparatus as viewed along the cutting plane 4—4 of those Figures.

FIG. 3 illustrates, in transparent outline, a typical square cross-section duct 110 for fluidized transport of air entrained cotton represented by the directional flow arrow 112. Along one duct boundary wall 104 is a sample depression 114 having a floor plane 116 between side walls 118. Set within the depression floor plane 116 is a transparent window 124 and a matrix 126 of apertures through the floor plane 116. Hinged between oppositely facing side walls 118 for rotation with an axle 136 parallel with the floor plane is a flapper element 130. Referring to the sectional view of FIG. 4, it is seen that the depression floor plane 116 is substantially spaced from the upstream face 132 of the flapper element 130 when the flapper is rotated out of the duct flow stream. Preferably, the downstream face 134 is substantially parallel with the plane of duct wall 104 when the flapper 130 is rotated out of the duct flow stream. Flapper rotation may be driven by any suitably controlled power means such as a linear strut motor not shown acting upon a crank arm 138.

As described by U.S. Pat. Nos. 5,087,120 and 5,639,955, the complete specifications of which are incorporated herein by reference, a sample quantity of cotton in the duct flow stream is quickly accumulated against the upstream face 132 of the flapper when raised transversely into the flow stream. Further rotation of the flapper presses the cotton sample accumulation into the depression 114 as a tightly compacted mass of cotton 128 against the window 124 and the aperture matrix 126. On the external side of the window 124 is an optical analysis instrument 150 for detecting cotton properties such as color and trash content. Suitable for this purpose are video camera based instruments made by Motion Control, Inc. and Zellweger Uster, Inc., such as is described in U.S. patent application Ser. No. 08/962,973 filed Oct. 28, 1997, the entirety of which is incorporated herein by reference. Light reflected from the cotton surface compacted against the interior window 124 surface stimulates electrical signals from the video camera 150. These signals, or an adjusted form thereof, are transmitted to the computer 200 as raw input data having proportional relevance to the cotton color and trash content.

Bonded to the floor 116 of the depression 114 is an electrically charged grid 140 comprising at least two parallel conductor circuits. The conductor elements are uninsulated for intimate electrical contact with cotton accumulations against the upstream face 132 of the flapper 130 when the flapper is rotated to compress the accumulation against the grid 140. Leakage current between the parallel circuits is conducted by the compacted cotton sample as a variable resistance. The resistance value of the cotton sample 128 is proportional to the cotton sample moisture content. At a known voltage potential between the parallel circuits, the sample moisture content is proportional to the corresponding circuit current flow. Values for the current flow are therefore transmitted to the computer 200 as sample moisture data.

In an alternative embodiment, the parallel conductor circuits for moisture content sensing may be bonded against the upstream face 132 of the flapper 130. The moisture sensor is more completely described in U.S. patent application Ser. No. 08/963,855 filed Nov. 4, 1997, the entirety of which is incorporated herein by reference.

Cotton sample accumulations 128 against the upstream face 132 of the flapper 130 that are compacted into the depression 114 by rotation of the flapper also are compacted against the aperture matrix 126. Resultantly, lenticular bulges 142 of fiber protrude from the external side of the aperture plate 126. With respect to FIGS. 4 and 9, a closed course conveyor or such as an endless carrier belt 160 having a plurality of comb devices 162 secured thereto is coursed around a plurality of sprockets 164. Each comb is constructed with a rotatable tine carrier as described by U.S. Pat. No. 5,178,007. This carrier belt is secured to the ducting 110 or other rigid framing structure to align the comb 162 traveling route into close proximity with the external face of the aperture plate and the matrix of cotton bulges 142. Movement of the combs 162 drives the extended tines through the protruding cotton bulges 142 to rake out a subsample of cotton fiber.

This subsample is characterized as a "beard" due to the physical appearance as an elongated, thin, flat, cluster of various fiber lengths. Preferably, carrier belt movement is intermittent with each increment of the belt traveling distance being coordinated to the minimum separation distances between several beard preparation and testing stations 166, 168, 170, and 172. Placement spacing between successive belt combs 162 along the carrier belt preferably corresponds to the belt movement interval. The stationary or standing interval between carrier belt movements is determined by the greatest beard sample processing time among the plural sequence. Normally, the standing interval is determined by the time required for a full cycle of the length/strength test instrument 170. Movement of the carrier belt 160 is driven by a motor not shown coupled to one of the belt carrier sprockets 164. Operational control over the belt drive motor may be by the central computer 200 but not necessarily so. Operation of the belt 160 is essentially independent of the computer 200 operation except for transmission of fiber property data to the computer 200.

Sample gathering by the flapper 130 also is an intermittent operation that includes a sample purging phase. Following at least one video scan of a compacted cotton sample 128 and the raking of at least one subsample beard, the flapper 130 is rotated away from the compacted sample 128 and into a downstream streamlining depression 144. Normal boundary layer turbulence and aspiration induced by the duct flow mainstream 112 purges the compacted sample 128 from the sample depression 114 and off the upstream face 132 of the flapper 130.

Representative samples of the main duct flow stream 112 for the micronaire test are preferably extracted by a shunting duct 180 depicted in FIG. 3. There are many well known techniques for inducing a small flow stream departure from a larger flow stream and most will include a partial vacuum or lower absolute pressure zone in the shunt duct 180 near its junction 182 with the main duct 100. In the example of FIG. 3, erection of the flapper 130 creates a localized static pressure increase in the main flow stream proximate of the junction 182. A small, induced exit draft along the shunting duct 180 away from the junction 182 will draw cotton particles out of the main flow stream into the shunting duct 180. A steady draft source for the shunting duct 180 is conveniently controlled by a disc valve 184 in the shunting duct flow channel. The disc axle shaft may be rotated, for example, by a crank arm 186 and a linear motor not shown.

Figure 21:
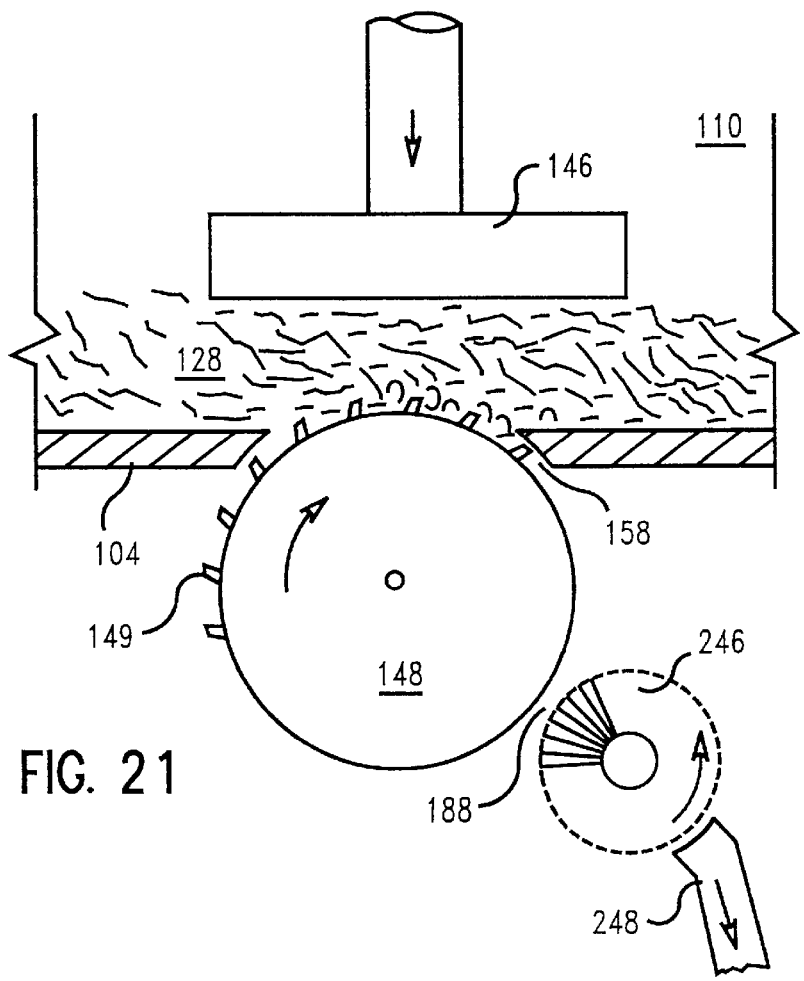
FIG. 21 is an elevational schematic of a first alternative sample extraction device.

One alternative sample extraction method and apparatus for the micronaire test or others is represented by FIG. 21. A cotton sample accumulation 128 within the transport duct 110 is compressed by any suitable means such as a reversing tamper 146 that presses the cotton bed 128 against the rotating tines or teeth 149 of a carding cylinder 148. A slotted aperture 158 in the duct wall 104 provides a shallow penetration of the tooth 149 perimeter into the accumulated cotton bed 128. Fiber snagged by the teeth 149 from the accumulation bed 128 is carried by the teeth 149 around the rotational arc of the carding cylinder 148 into a rotating nip 188 with a rotary brush 246. Here, the more rapidly rotating rotary brush 246 extracts the samples from the card cylinder teeth. A vacuum pipe 248 having a pickup opening adjacent to the brush 246 perimeter drafts the fiber held by the brush bristle into the pipe for delivery into the micronaire test chamber.

In alternate embodiments, the cotton sample is not acquired and delivered automatically from the cotton feed stream in the gin to the test equipment. In these alternate embodiments, the cotton sample is obtained in some other manner and delivered to a stand-alone piece of test equipment. The stand-alone test station may house all or any one of a number of different combinations of the instrumentation described herein, including the testers for fiber length, fiber length distribution, fiber strength, fiber elongation, fiber moisture content, fiber trash content, fiber trash identification, fiber color, fiber color distribution, fiber micronaire, and fiber maturity. Preferably, the stand-alone test station includes test stations for fiber length, fiber moisture, and fiber color.

Figure 26:
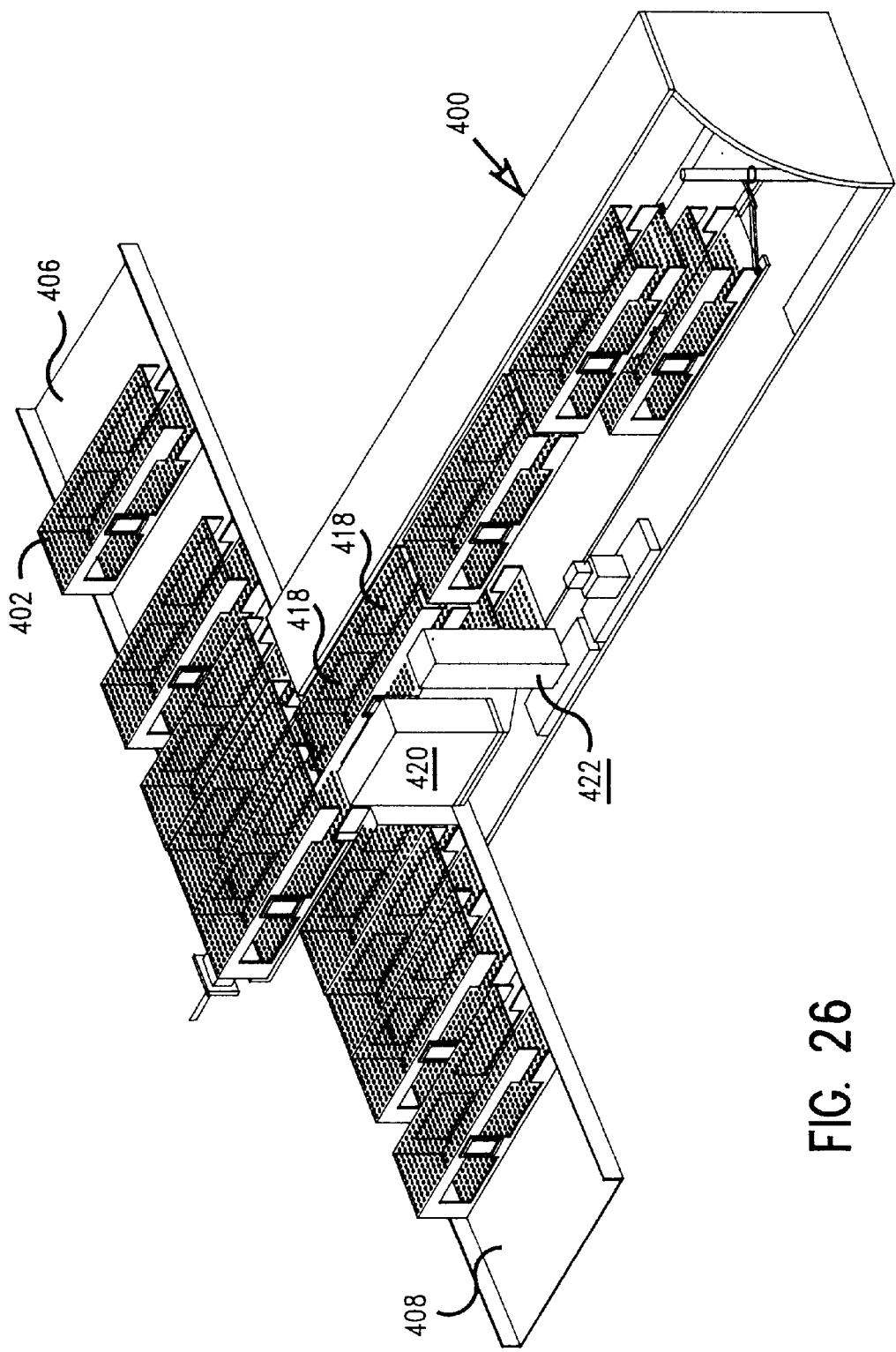
FIG. 26 is a perspective view of a semi-automated stand alone testing apparatus.
Figure 27:
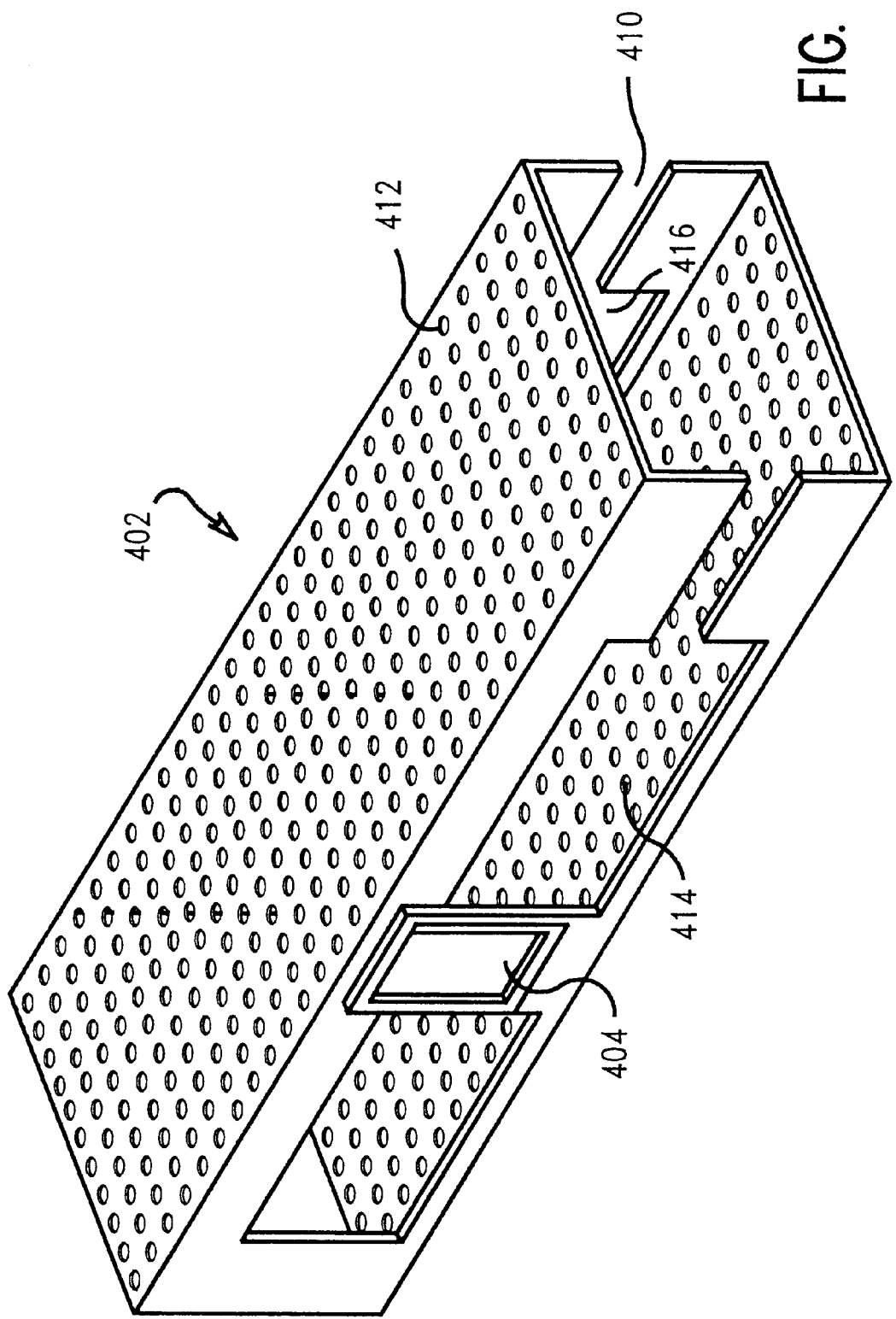
FIG. 27 is a perspective view of a cassette for a semi-automated stand alone testing apparatus.
Figure 28A:
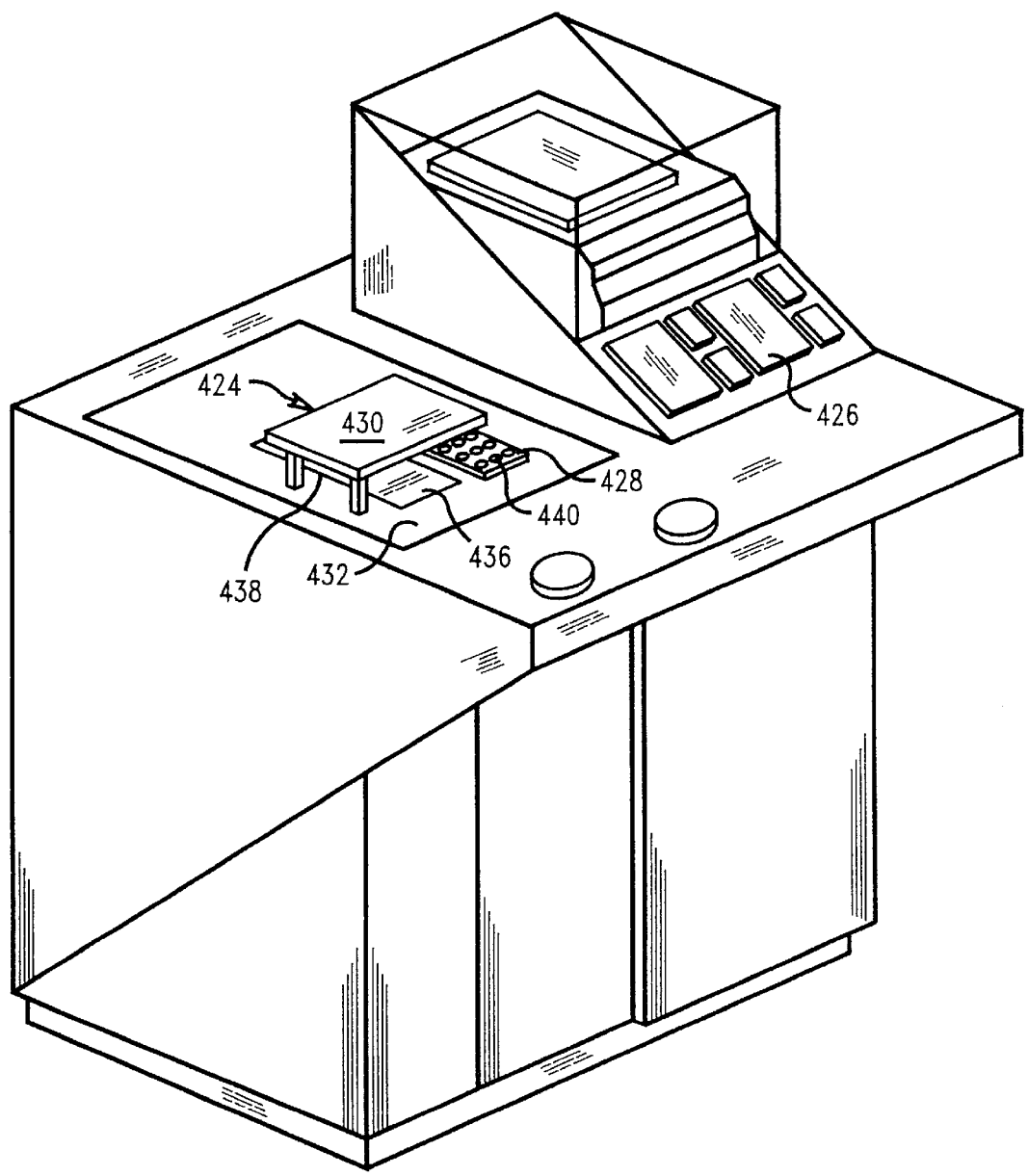
FIGS. 28A–28D are perspective and plan views of a manual stand alone testing apparatus.
Figure 28B:
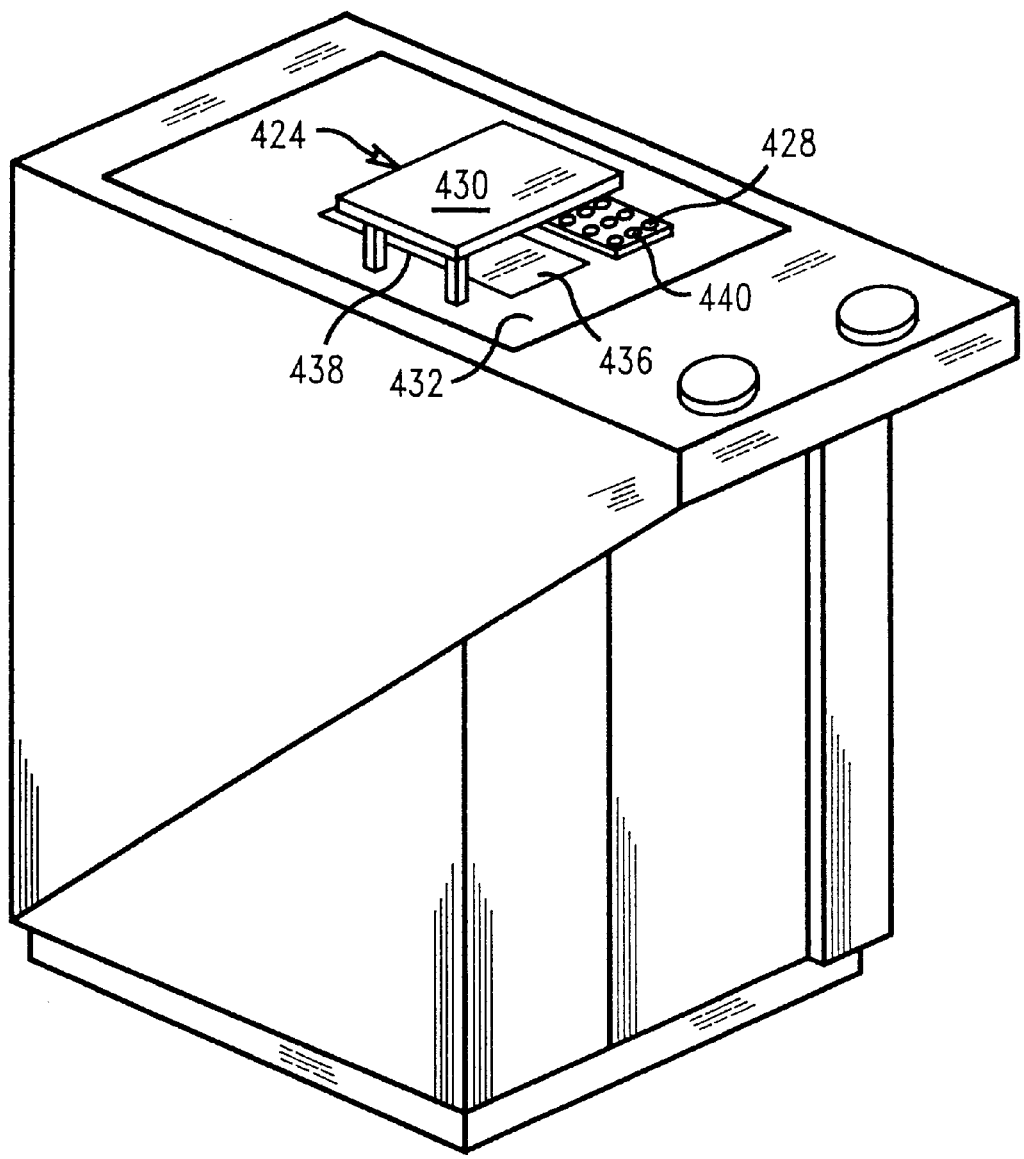
Figure 28C:
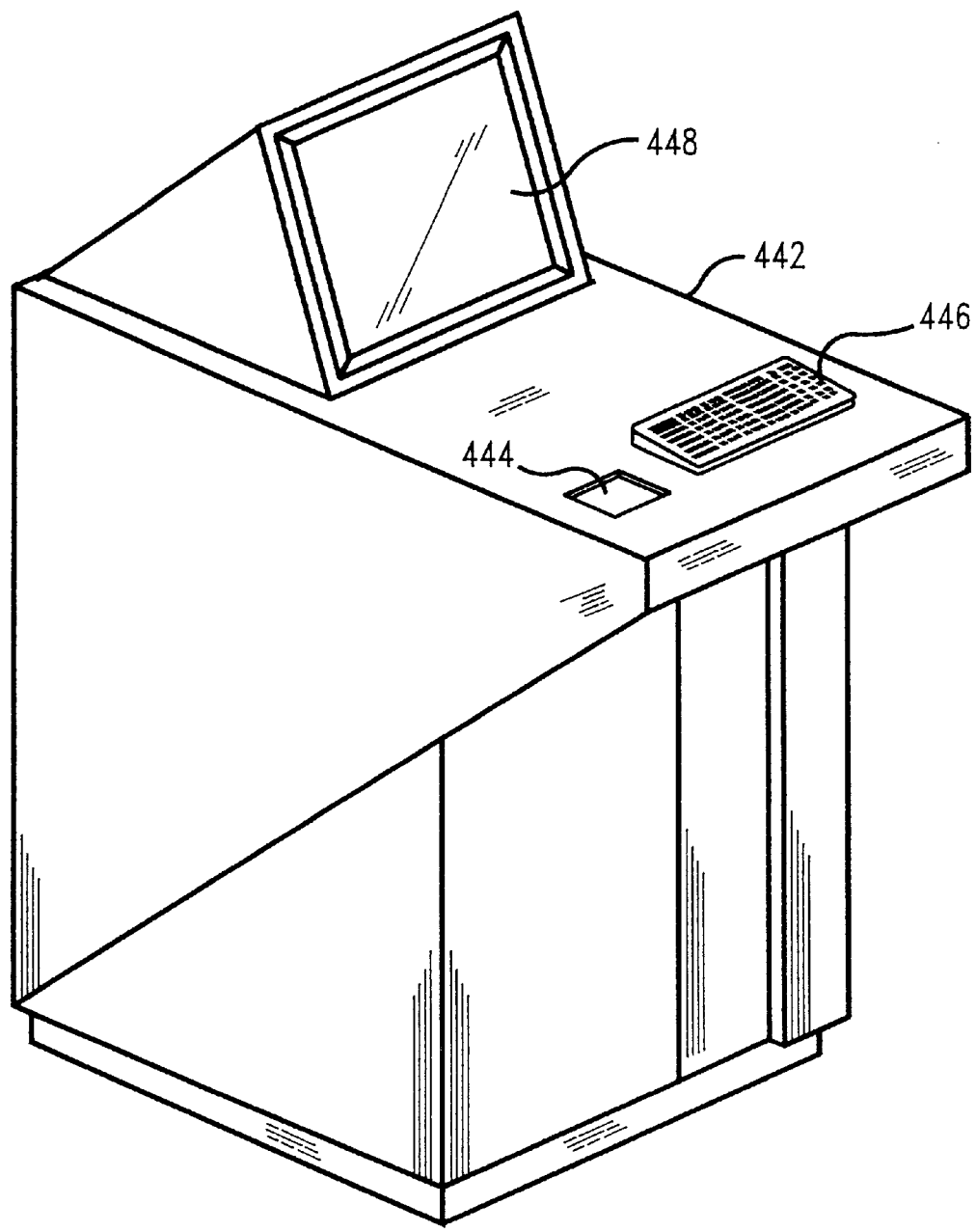
Figure 28D:
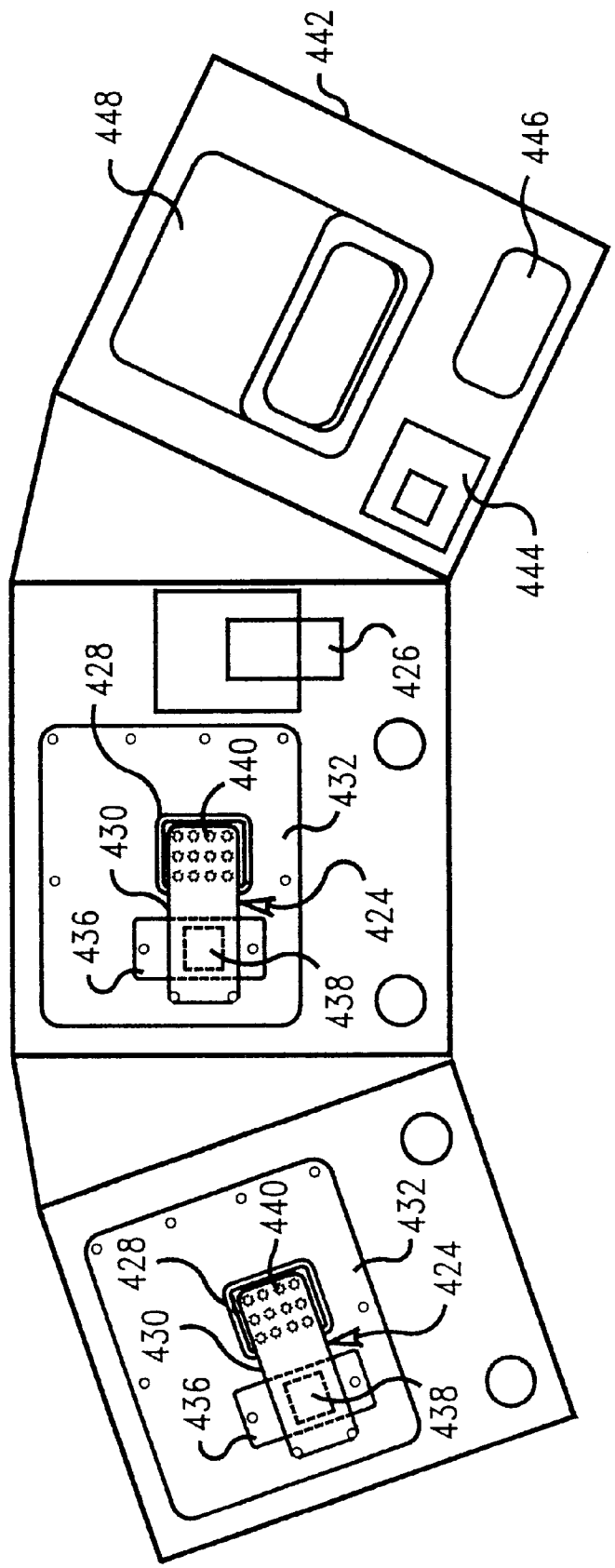

In one embodiment, depicted in FIG. 26, large samples of cotton are acquired and brought to the test station 400 in bins or cassettes 402, such as depicted in FIG. 27. The bins or cassettes 402 preferably include some sort of identifier so that each bin or cassette 402 can be uniquely identified by the test station 400. One method of accomplishing this is to have a removable bar code label 404 on each bin or cassette 402, that is scanned by the test station 400 and to which all of the measurements taken by the test station 400 are correlated. The bins or cassettes 402 are loaded into an automated staging and indexing system, such as on a moving conveyor belt 406. In this manner, bins or cassettes 402 containing new cotton samples can be brought to the test station 400 and loaded while the test station 400 is still busy taking measurements on a previously loaded bin or cassette 402. When the readings on the current bin or cassette 402 are concluded, the staging and indexing system is incremented, bringing the next bin or cassette 402 into a position when the cotton sample within it can be measured, while the previous cassette is placed onto an output means, such as another moving conveyor belt 408. The previously measured cotton sample is automatically moved to a holding station, from which it can be removed at a later point in time.

Figure 24:
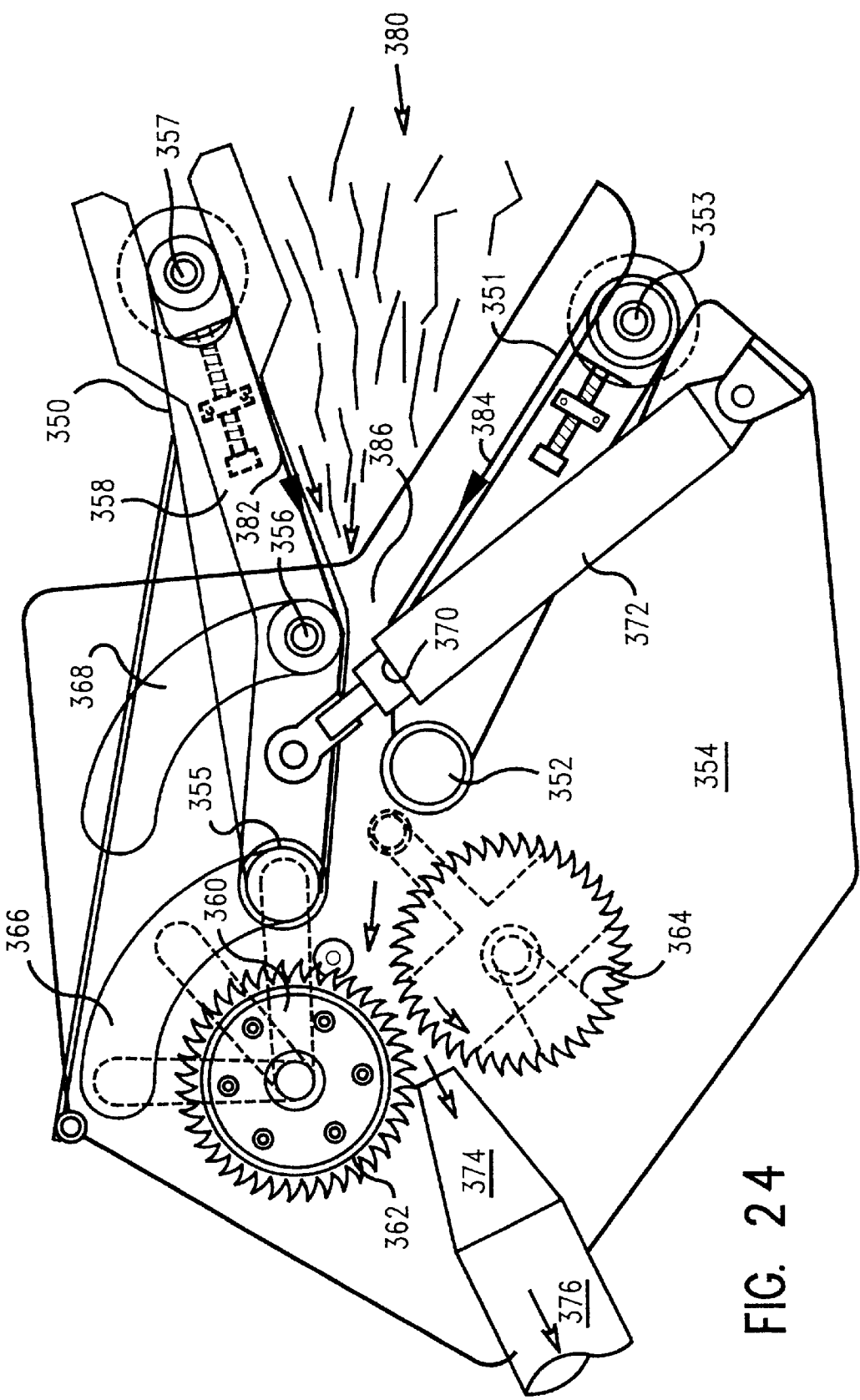
FIG. 24 is an elevational schematic of a second alternative sample extraction device.

In this embodiment, subsamples are preferably acquired from the cotton sample contained within the bin or cassette 402. In the process of acquiring the subsamples, the cotton sample is preferably more fully opened. In other words, the process of acquiring the subsample tends to individualize the fibers within the cotton sample to a greater degree. One such sample extraction apparatus is illustrated in FIG. 24 and comprises a pair of closed belt circuits 350 and 351 driven in opposite circulation directions. The segment 382 of the belt 350 circuit cooperates with the segment 384 of the belt 351 circuit to delineate the boundaries of a fiber capture zone 380 therebetween. Traveling in opposite directions about respective circuits, these belt segments 382 and 384 converge upon a mutual throat zone 386.

Belt 351 is driven about carrier rollers, including 352 and 353, having fixed position axes relative to the frame plates 354. The rotational axes of carrier rollers 355, 356 and 357, however, are secured to a translation arm 358. The rotational axis of carrier roller 355 is also restrained by a swing link 360 having an opposite end rotational axis common with that of a carding cylinder 362. The rotational axes of carrier rolls 355 and 350 are also confined to guide slot paths 366 and 368 secured to the frame plates 354. Translation movement of the translation arm 358 responds to the extension of rod 370 from the cylinder 372. Such extension of the rod 370 translates the belt circuit 350 about the axis of carding cylinder 362 while the guide slots 366 and 368 sustain the orientation of the belt circuit 350 relative to the belt circuit 351. Such translation selectively adjusts the sample capture zone 380 volume between the belt circuits for consolidating cotton particles into the throat area 386 therebetween. This throat area 386 discharges into the rotating convergence between carding cylinders 362 and 364. Emerging from the carding cylinder convergence, the fully opened cotton particles are drafted into a vacuum nozzle 374 for transport via discharge duct 376 to a micronaire measurement chamber or other cotton property test instrument, such a cotton maturity test station.

In an alternate embodiment, the subsamples for the micronaire and maturity test stations are acquired by the carding and doffing apparatus as described more particularly elsewhere herein, and as depicted in FIG. 21.

Preferably, the fiber subsamples for the fiber length, length distribution, strength, and elongation test stations 422 are acquired using a comb sampler on a circuitous belt, such as is described elsewhere herein with greater particularity. The combs contact the cotton within the cassette 402 in one or more of several different ways. For example, the combs can contact the cotton through a slot 410 in the top, bottom, or sides of the cassette 402. Alternately, the combs can remove the cotton subsample from apertures 412 in the top, bottom, or sides of the cassette 402, where the cotton is pressed through the apertures 412 by a ram 418 entering the cassette 402 from the other side.

The subsamples for the fiber color, color distribution, trash content, and trash identification are preferably acquired by compressing the fiber sample within the cassette 402 with a ram 418 that enters through a port 414 on one side of the cassette 402, and presses the cotton subsample against a transparent plate of the cotton property test station 420, which is disposed adjacent a second port 416 on the opposite side of the cassette 402. The fiber moisture sensing station is disposed adjacent the transparent plate in one embodiment, and in the end of the ram 418 in another.

In yet another embodiment, depicted in FIG. 28A–28D, the stand-alone test equipment does not acquire subsamples from a bin or cassette 402. In this embodiment, the subsamples are prepared in another manner, such as by manually opening the cotton samples and placing them individually adjacent or within the testing surfaces or chambers where the measurements are taken. For example, the sample for the moisture content reading is placed into contact with the moisture sensor arrays 424, and the sample for the micronaire reading is placed within the micronaire chamber 426. Further, the sample for the length, strength, elongation, and fiber length distribution reading is placed on top of an aperture grid 428 where a comb can acquire the subsample. Thus, this is a more manual embodiment of the invention, which might be used in a gin having a lower volume of production, or in a gin where the raw cotton has very uniform properties over time so that the fully automated control of the other embodiments is not required.

In a preferred configuration of this embodiment, a fiber containment means, such as a moving plate 430, compacts and confines a fiber sample in a stationary fashion between the plate 430 and a perimeter wall, such as a test surface 432. The fiber moisture testing station 424 may be located either in the moving plate 430 or on the test surface 432. The fiber color testing station 436 is preferably disposed adjacent a transparent optical window 438 within a portion of the test surface 432.

An aperture plate 428 is preferably disposed adjacent the optical window 438 in the test surface 432. The moving plate 430 presses a portion of the cotton sample through the apertures 440. This portion of the cotton sample is engaged by a comb on the other side of the aperture plate 428, and taken to a fiber testing station, such as a fiber length testing station. The comb may be a part of a circuitous sampler, described with more particularity elsewhere herein. Alternately, the comb may be a single comb that travels along a path to grooming stations and then to the testing station, and then returns along the same path to acquire another subsample. In the preferred embodiment, the comb is moved relative to the cotton sample, which is held stationary in reference to the rest of the testing apparatus. Thus, the subsampling comb moves relative to the rest of the testing apparatus. This greatly simplifies the mechanical operation of the subsampling process, and allows for the other tests, such as moisture content and trash content, to be concurrently performed on portions of the same fiber sample from which the fiber length subsample is taken.

A console 442 is used to enter identifying and other information about the fiber sample being testing. The information may be entered on a keyboard 446 or by a bar code reader 444. The information and test results are presented on a display 448.

Duct Flow Routing

Viewing FIGS. 5 and 6 together, a typical duct flow routing apparatus is shown to serve the saw lint cleaner 82I. The same duct flow routing principles described hereafter with respect to the lint cleaner 82I are also applicable to the other material processing and conditioning machines in the gin system such as the dryers and green boll separators.

For the example selected, transitional ducts 106I and 108I connect the flow controller body 100I (4-way valve) to the main flow stream duct 110I. Between the junctions with the main duct 101 respective to the transitional ducts 106I and 108I is a duct flow gate 196I rotated about an operational quadrant by a linear motor 197I. Deployment of the flow gate 196I blocks the main flow stream between an upstream duct section 110I and a downstream duct section 110J. When the flow gate 196I is deployed to block flow between duct sections 110I and 110J, linear motor 199I operates to rotate the flow gate 198I to a position of open flow connection between the upstream duct section 110I and the inlet transitional duct 106I. Additionally, linear motor 194I operates to position the flow controller switch plate 190I for isolation of the inlet flow stream from the exit flow stream. Accordingly, the cotton entrained flow stream arriving along duct section 110I is guided into the transitional duct 106I and finally into the lint condenser supply chute 81I. Coming out of the lint cleaner 82I, discharge duct 86I transports the flow stream back to the flow controller 100I and from there into the discharge transitional duct 108I for return into the downstream section 110J of the mainstream duct.

In the alternative condition, the duct flow routing apparatus of FIGS. 5 and 6 rotates the mainstream flow gate 196I to open the main flow stream duct between the upstream duct section 110I and the downstream duct section 110J. Simultaneously, flow gate 198I is rotated to close the juncture opening between the upstream duct section 110I and the transitional inlet duct 106I. Although mainstream flow into the cleaner 82I is blocked by flow gate 198I, it is essential that the process machine be isolated from the main transport duct 110J for purposes of draft power management. Hence, the flow switch plate is rotated to the closure position that isolates the cleaner inlet and discharge ducts 81I and 86I from the flow controller outlet 108I and the main duct 110J.

Figure 7:
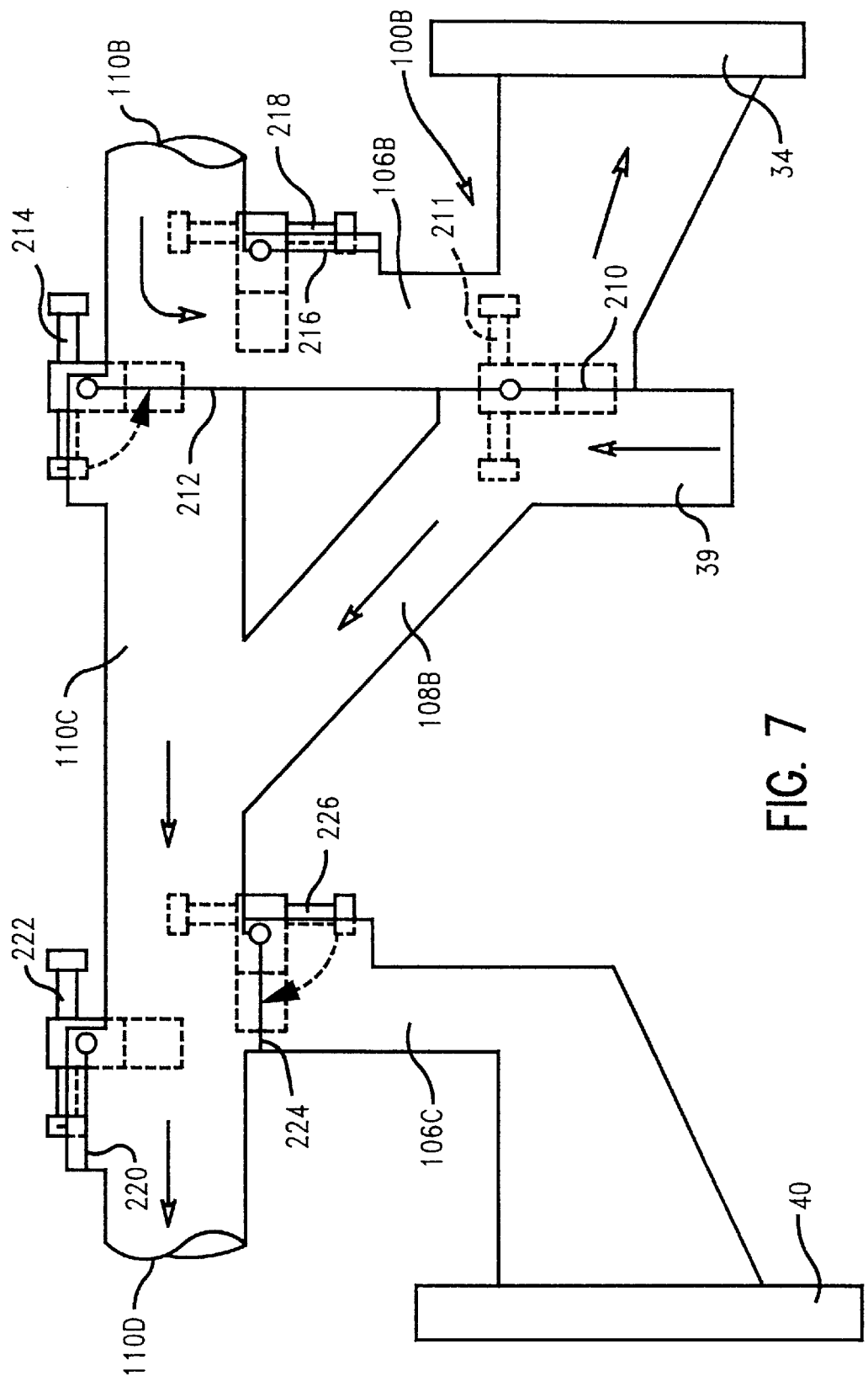
FIG. 7 is a schematic representation of a second type of duct flow control apparatus applicable to the present invention.

An alternate embodiment of the automated flow control for the present invention is schematically illustrated by FIG. 7. In this embodiment, closure of the flow gate 212 by rotary actuator 214 isolates an upstream section 110B of the main flow stream from a downstream section 110C. Coordinately, remotely controlled rotary actuator 218 positions the flow gate 216 to open a passageway from the mainstream duct 110B into the flow controller inlet 106B. Additionally, remotely controlled rotary actuator 211 positions the flow switch plate 210 of the 4-way valve 100B to isolate the flow stream into the inclined cylinder cleaner 34 from the discharge flow stream 39. Simultaneously, 4-way valve 100B connects the cylinder cleaner discharge duct with the valve discharge conduit 108B and the downstream section 1 IC of the main flow stream.

Should it be determined by the material property test data that processing the material flow stream through the stick and green leaf cleaner 40 is unnecessary and undesirable, remotely controlled rotary actuator 226 operates the flow gate 224 to close the machine 40 inlet duct 106C from the main flow stream 110C. Flow gate 220 is operated by rotary actuator 222 to open the mainstream flow section 110C to the next successive flow section 110D.

Figure 8:
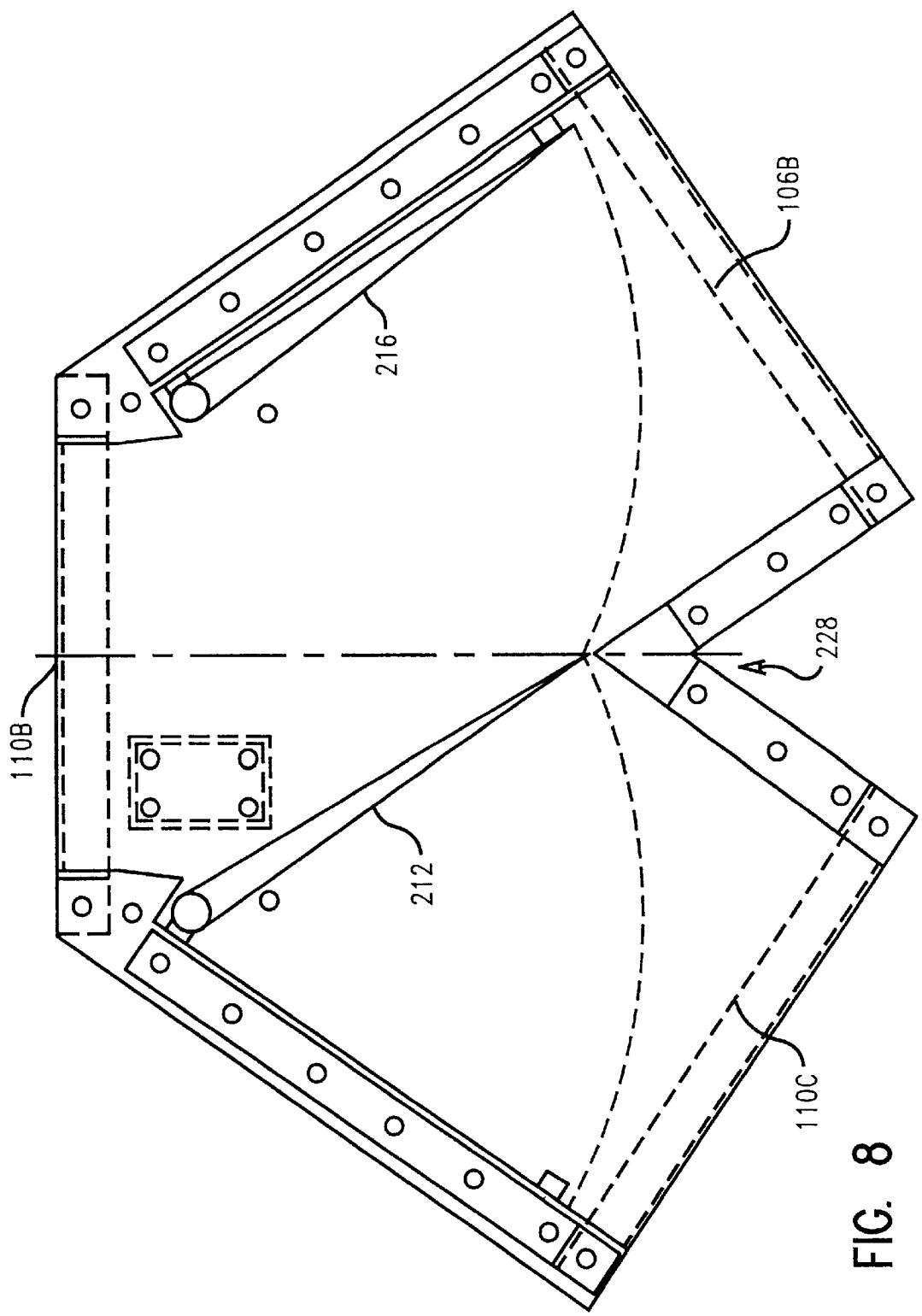
FIG. 8 is a schematic representation of a third type of duct flow control apparatus applicable to the present invention.

The FIG. 8 invention embodiment engages a Y-joint section 228 of ducting at the juncture of the flow controller inlet 106B with the mainstream duct 110. In this embodiment of the invention, flow gates 212 and 216 swing substantially in parallel and therefore may be operated by a single actuator.

Length and Strength Fiber Testing

Referring again to FIG. 9, the first increment of belt movement following extraction of a fiber subsample beard 161 by a carrier belt comb 162, stops the belt comb in front of a first grooming station 166. This first grooming station 166 preferably comprises a rotary carding cylinder 167 having stiff wire bristles to rectify the individual fibers of a beard and remove entangled fiber clusters called "neps." An air draft may be drawn over the rotating carding cylinder to cleanse the cylinder bristles of neps and loose fiber.

A second advancement increment of the carrier belt positions the belt carried comb holding the carded beard 161 in alignment with the translation path of a rotary brushing station 168. The brushing station 168 is mounted on linear bearings 169 for controlled movement driven by a second stepping motor not shown between an operative position most proximate of the belt carried comb 162 and an inoperative position that is more remote from the comb 162 path of movement. The previously carded beard is now drawn into a nip between a finer, pliable bristle rotary brush 154 and a cooperative plate 156. When the brushing interval is complete, the brushing station 168 is withdrawn from the belt along the translation path determined by the linear bearing 169.

The third advancement increment of the carrier belt 160 aligns the combed and brushed beard 161 projecting from the belt carried comb 162 with a specimen slot 230 (not depicted in FIG. 9) in the length/strength tester 170. As a unit, the length/strength tester 170 is reciprocated along a linear bearing 176 by a third stepping motor, also not shown. With respect to FIGS. 10 through 16, the tester 170 is enclosed by a housing having a front wall plate 232. With particular reference to FIG. 14, the housing front wall plate supports a rigid, light guide plate 233 with a "floating" mount that permits the glass light guide 233 a limited degree of independent movement relative to the front wall plate 232. A slot 230 in the guide plate 233 divides the plate between an upper light guide section 234 and a lower light guide section 236. The upper edge 238 of the glass upper light guide section 234 is a diffusive light receptor having a frosted, concave surface. Along the focal axis of the receptor concavity is an array of multiple light emitting diodes (LED) 240. Along the lower edge of the lower light guide 236 is an elongated, large area photo sensor 242. The critically sensitive elements of this light sensor are relatively fixed for alignment maintenance therefore. A draft pipe 244 draws air from within the housing to stimulate an air draft into the beard slot 230. As the tester front wall advances by rotation of the stepping motor along the linear bearing 176 toward the carrier belt, the air draft into the slot 230 assures penetration of the slot 230 by the beard 161.

Penetration of the slot 230 by the beard 161 blocks a calibrated light transmission from the upper light guide 234 into the lower light guide 236 thereby influencing the signal values emitted by the photo sensor 242. By coordinating the photo sensor signal values to the position of the tester unit 170 as the beard progresses into the slot 230, both the greatest fiber length and fiber length variation may be determined for the beard constituency. The angular positioning of the stepping motor drive signals the relative location of the testing unit 170 to the tester control program with great precision. Fiber length and fiber length variation values respective to each beard subsample extracted from the material mainstream are combined with a predetermined number of preceding values to generate a representative average value.

It will be useful to review the data acquired from a sample beard by the length/strength test instrument. As the beard advances between the upper and lower light guides, the initial reduction in light transmission across the slot 230 detected by the photo sensor 242 signals arrival of the leading edge of the longest fiber in the beard. This arrival signal is correlated to the simultaneous stepping motor signal for a positional reference point. This correlation continues until the photo sensor 242 signals remain substantially unchanging as beard penetration continues. The stepping motor signal at this positional point is noted by the control program to resolve a linear differential between the leading edge reference point and the signal stabilization point. It is inferred from the stable photo sensor signal that all fibers in the beard are at least long enough to interrupt the slot 230 light transmission. Consequently, this position location of the slot designates the shortest fiber in the beard. Notwithstanding further penetration of the beard into the slot, no additional light transmission is lost. The linear distance between the reference point and the stabilization point, therefore, is the fiber length variation.

The foregoing procedure may be expanded with an iterative calculus to correlate intermediate slot positions between the reference point and the stabilization point to a magnitude or percentage of light reduction respective to each linear increment in the overall differential for a length distribution appraisal.

With the testing unit 170 at the most proximate location relative to the belt carried comb 162, the beard 161 is at a position of penetration into the slot 230 that passes the beard between two pair of vise jaws 250 and 252 (FIG. 16). Vise 250 has a fixed position with respect to a testing unit 170 frame supported by the linear bearing 176. Vise 252 is provided reciprocal movement with respect to the fixed position vise 250. The reciprocating movement of vise 252 is parallel with the linear bearing 176 movement. Fixed position vise 250 comprises a fixed position lower jaw 250b and a moving upper jaw 250a. Two laterally balanced pairs of air cylinders 260 are secured to the fixed position lower jaw 250b. Piston actuated rods 262 projecting from each cylinder 260 are secured to the moving upper jaw 250a of the fixed position vise 250. Opposed vise jaw bars 254a and 254b, secured to the moving upper jaw 250a and to the fixed position lower jaw 250b, respectively, are aligned with the plane of the beard slot 230 and when open, receive the beard 161 therebetween.

The moving vise 252 also comprises a fixed position lower jaw 252b and a moving upper jaw 252a. Air cylinders 264 are secured to the fixed position lower jaw 252b. Piston rods 266 projecting from the respective cylinders 264, are secured to a moving upper jaw 252a. Vise jaw bar 256a is secured to the moving upper jaw 252a above the beard penetration plane and vise jaw bar 256b is secured to the fixed position lower jaw 252b below the beard penetration plane.

A reciprocating transmission mechanism such as a jack screw or worm and rack secured to and between the lower jaw 250b of the fixed position vise 250 and the lower jaw 252b of the moving vise 252 is driven by a highly accurate stepping motor 174. A calibration magnet 268 secured to the lower jaw of the moving vise 252 cooperates with a calibration switch 269 to maintain the accuracy of relative displacement measurements between the fixed and moving vises implied from the angular position signals for the stepping motor. Additionally, the transmission mechanism is secured to the moving vise 252 through a load or force measuring cell 270. A floating joint 272 accommodates calibration adjustments between the load cell 270 and the moving vise 252.

Figure 9:
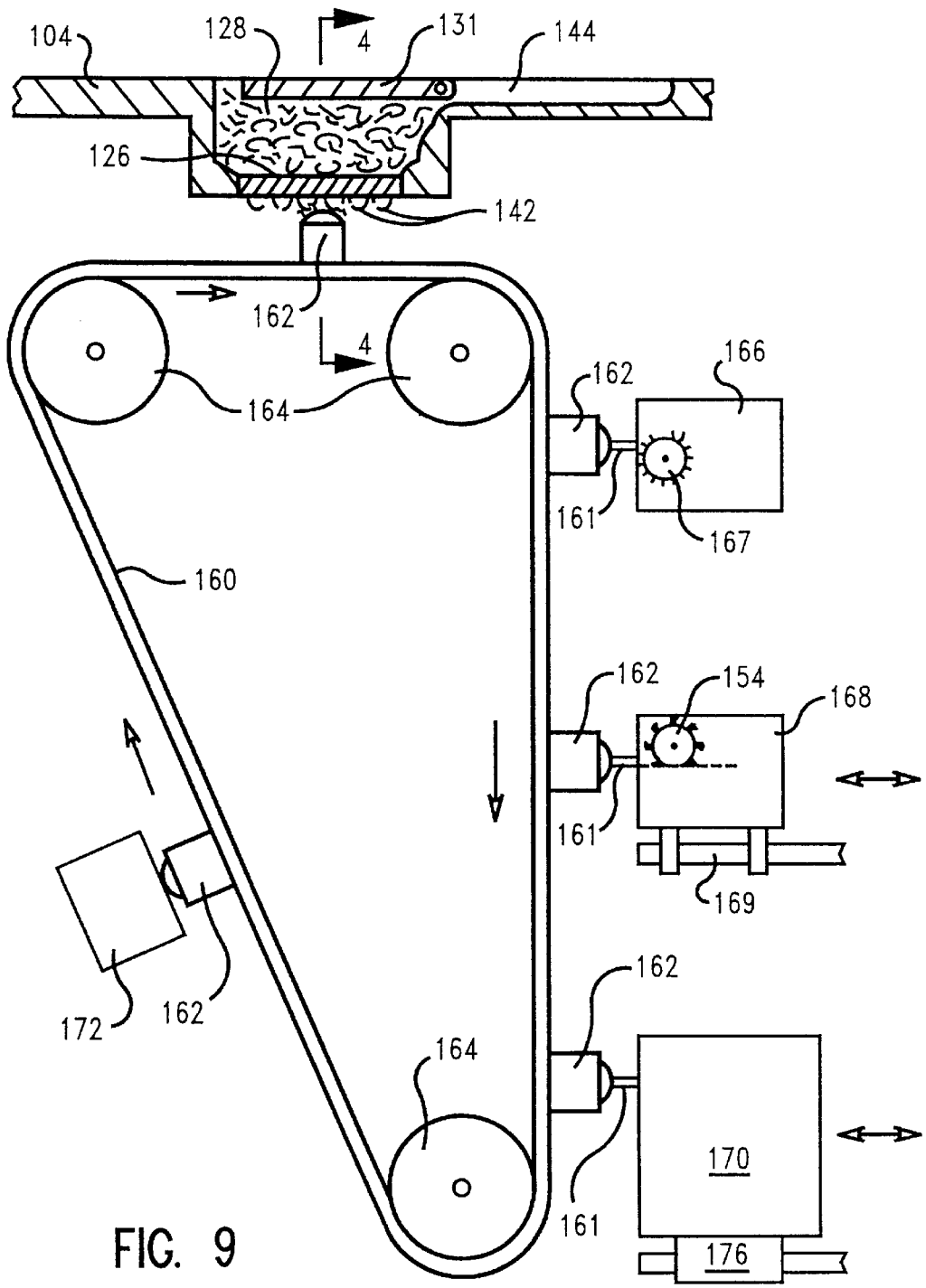
FIG. 9 is a mechanical schematic of the in-situ fiber length and strength sampling and testing apparatus for the present invention.
Figure 10:
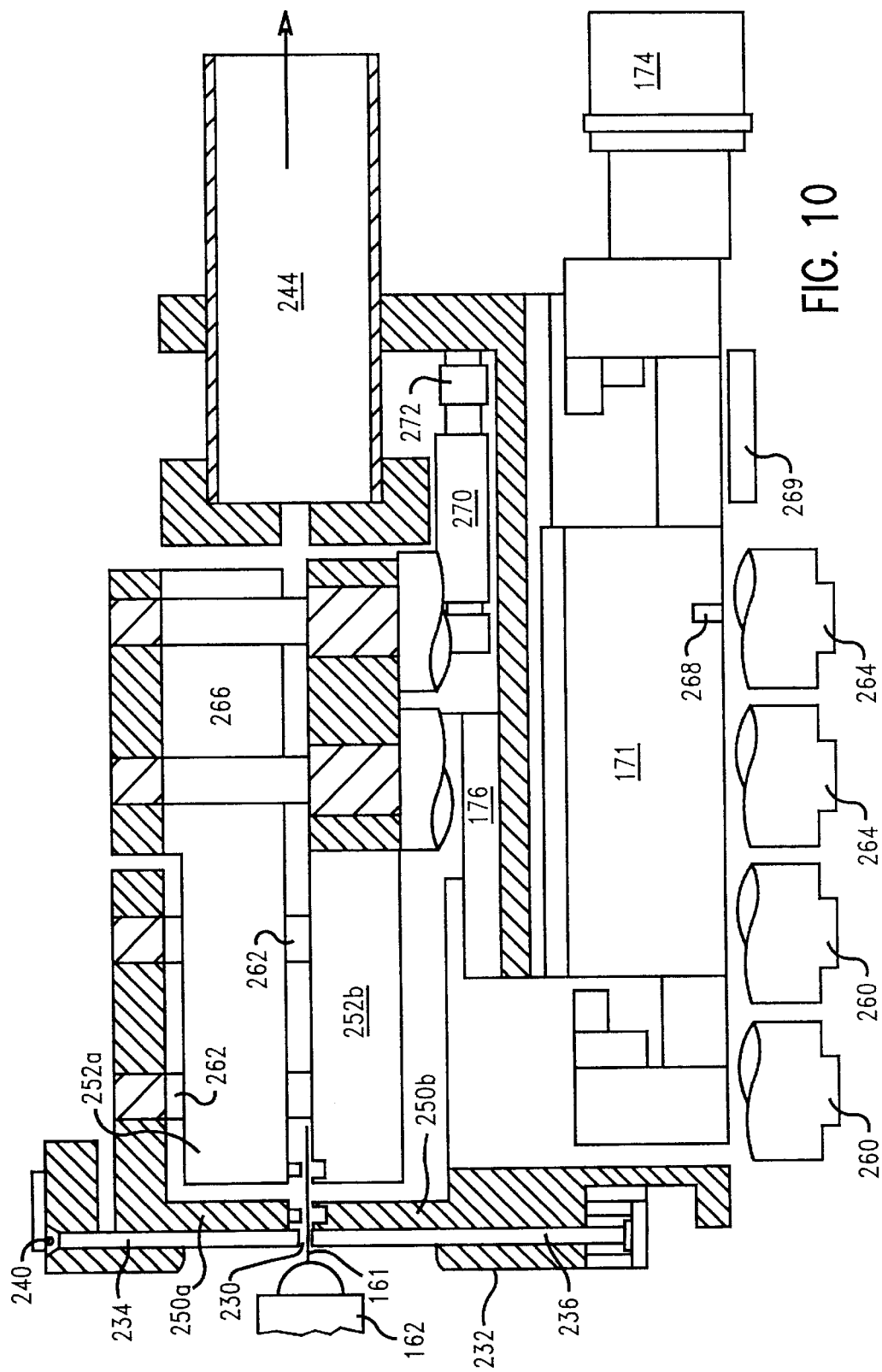
FIG. 10 is a cross-sectional side view of the fiber length and strength property testing apparatus of the present invention shown as a mechanical schematic format.
Figure 11:
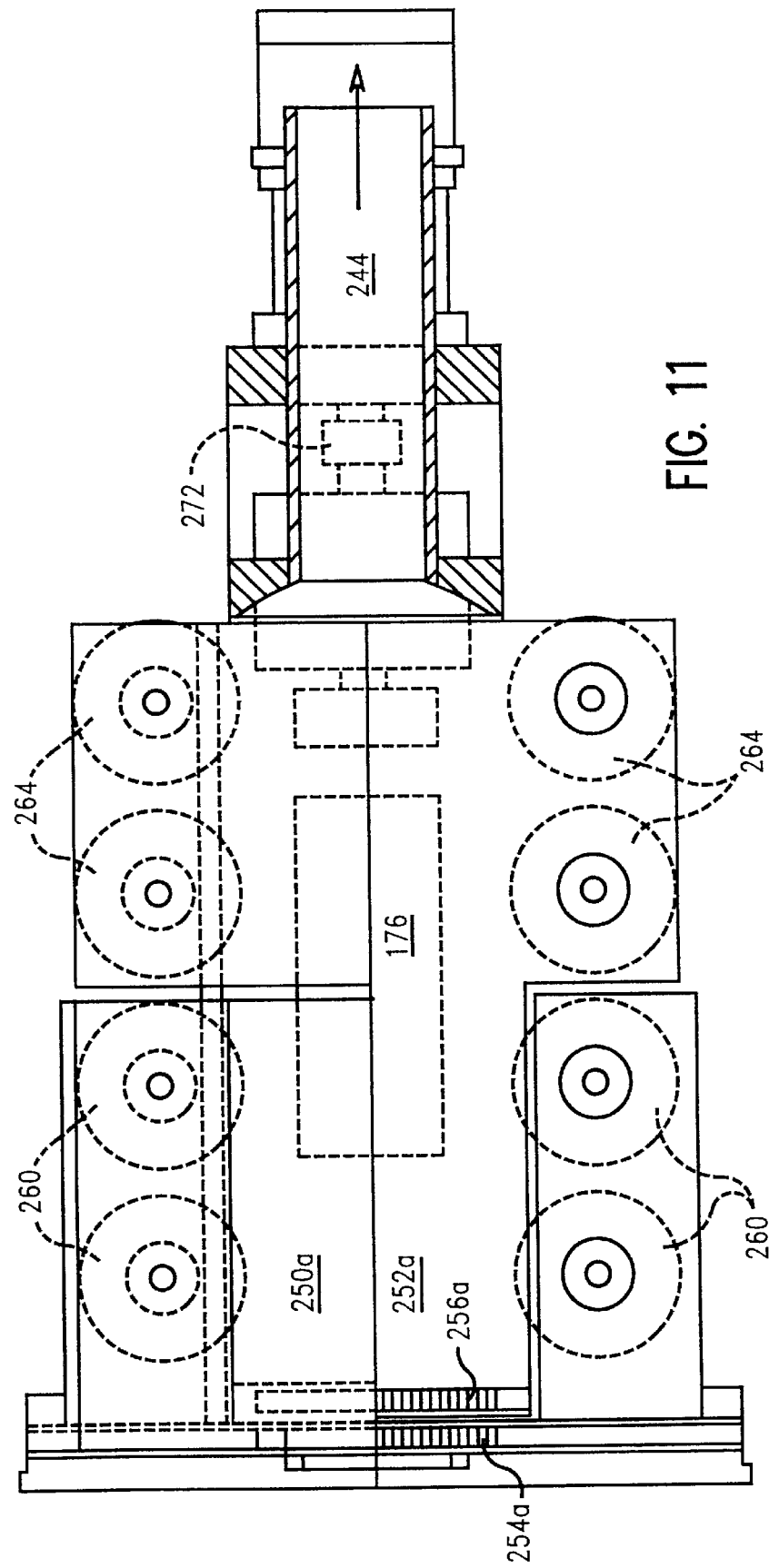
FIG. 11 is a partially sectioned top plan view of the length and strength property testing apparatus of the present invention shown as a mechanical schematic.
Figure 12:
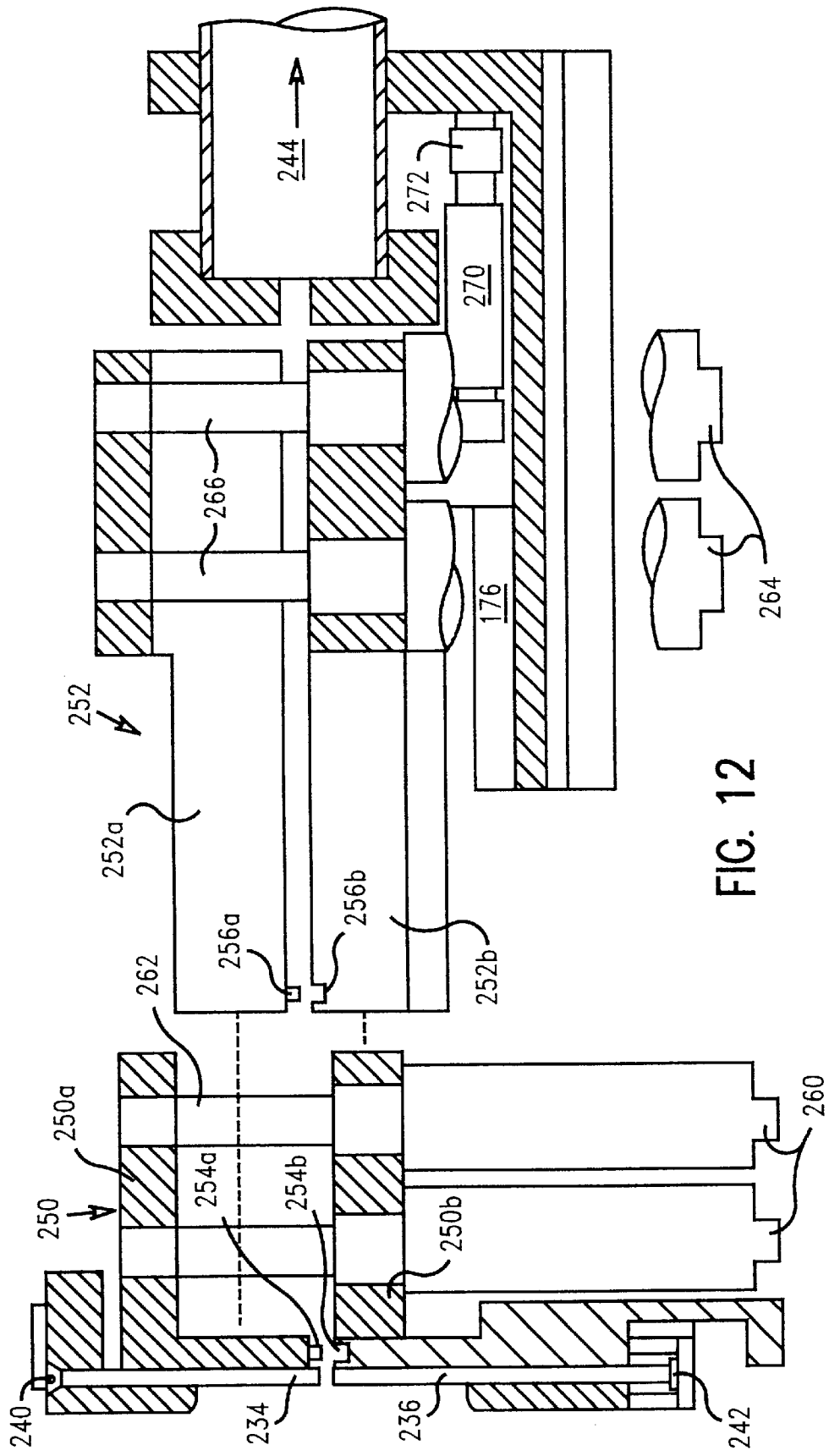
FIG. 12 is a cross-sectional side view of the fiber length and strength property testing apparatus of the present invention shown as an exploded mechanical schematic.
Figure 25:
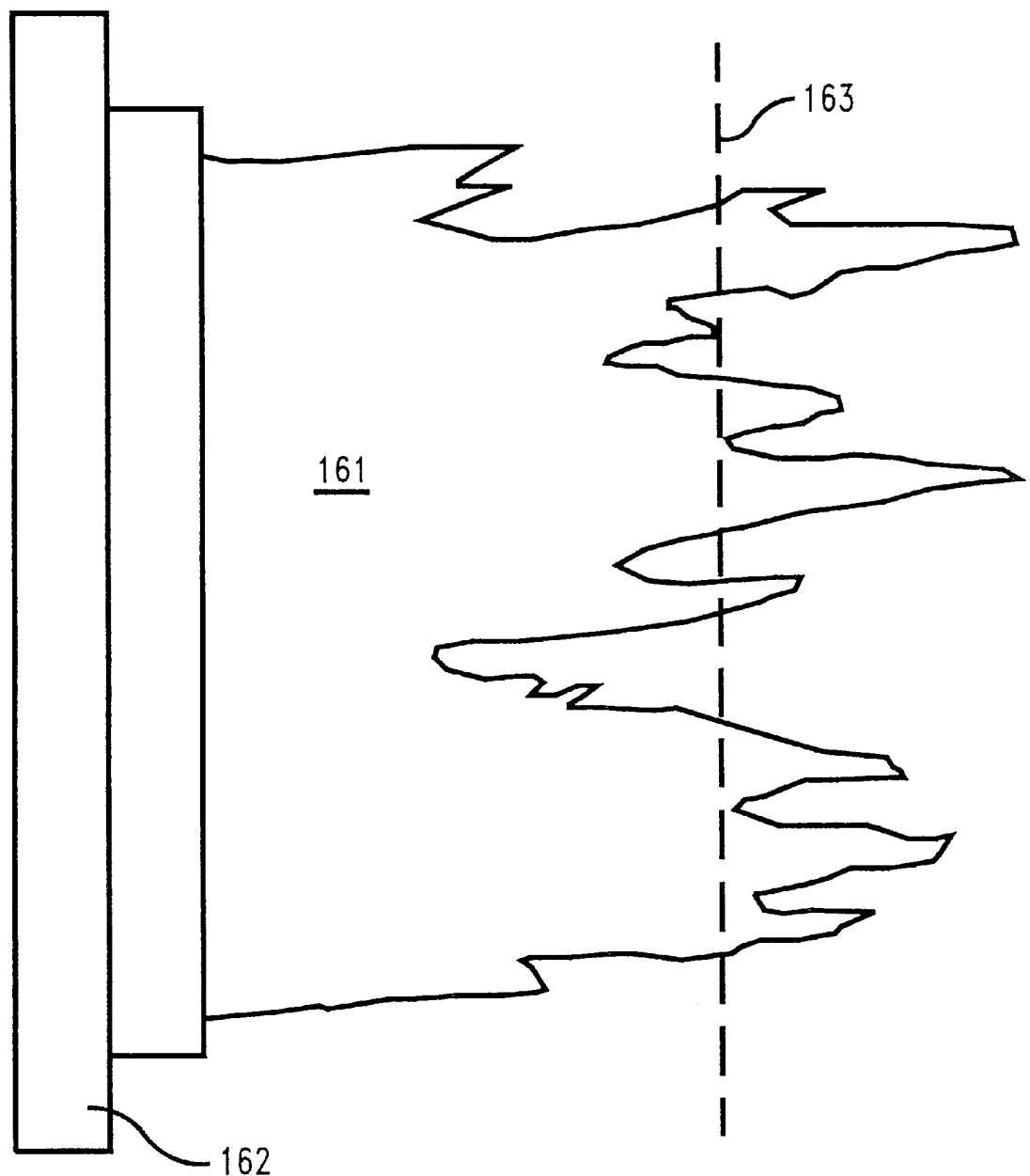
FIG. 25 is an enlarged representation of a beard sample prepared for testing.

For consistent and meaningful fiber elongation and strength measurement, it is preferable that the number of fibers subjected to failure stress be known or at least a consistent number isolated for measurement. From the length and length distribution data obtained from the light sensor, a beard 161 plan may be visualized as shown by FIG. 25. Within the beard plan, the position of a planar line 163 may be located relative to the reference plane. The position of this line 163 is selected to cross a predetermined total number of fibers, regardless of the fiber distribution sequence across the beard plan. The testing unit 170 position, therefore, is adjusted relative to the beard 161 to align the plane of line 163 between the beard clamping jaws 254 and 256. Here, the air cylinders 260 and 264 are charged with pressurized air to close the moving jaws 250a and 252a toward the respective stationary jaws 250b and 252b. Consequently, a substantially consistent number of fibers in the beard 161 is clamped between respective pairs of vise jaw bars 254 and 256. While clamped, the stepping motor 174 drives the transmission to separate the moving vise jaw set 252 from the fixed position vise jaws 250. A cumulative count of the stepping motor arc pulses multiplied by the transmission ratio determines the linear distance of the jaw pair separation with considerable precision. Simultaneous with the jaw separation, the load cell 270 senses and transmits to the control computer the force values required to continue the fiber elongation. This force monitored elongation of the subsample beard is continued until rupture. When the beard breaks between the two pairs of clamping bars 254 and 256, the value of fiber elongation and maximum strength has been determined. Thereafter, the control computer directs the vise cylinders to open. The severed beard end that had been clamped between clamping bars 256 is removed by the slot 230 draft through the draft pipe 244. The fore end of the beard 161 remains secured to the belt carried comb 162. As depicted in FIG. 9, a subsequent advancement of the belt 160 aligns the comb 162 with a beard disposal station 172. Here the fiber clamping mechanism of the comb 162 is opened and the beard residual is removed by the operation of a brush and vacuum.

Those of ordinary skill in the art will recognize the value in positioning the on-line length/strength measuring system of FIGS. 9–16 before and after the most critical cotton processing such as drying and ginning. In particular, it is useful to know if the average fiber length in a flow system is being reduced in transit through a set dryer sequence. Similarly, if fiber emerging from the gin stand suffers an average strength reduction, certain upstream process changes may be in order.

Micronaire Testing

Basis for a micronaire value is derived from Koxeny's equation which provides a credible approximation for the permeability of powders having a negligible number of "blind" pores. See The American Institute of Physics Handbook. This equation characterizes the relationship of air flow resistance over a surface with a known mass in a known volume.

Figure 17:
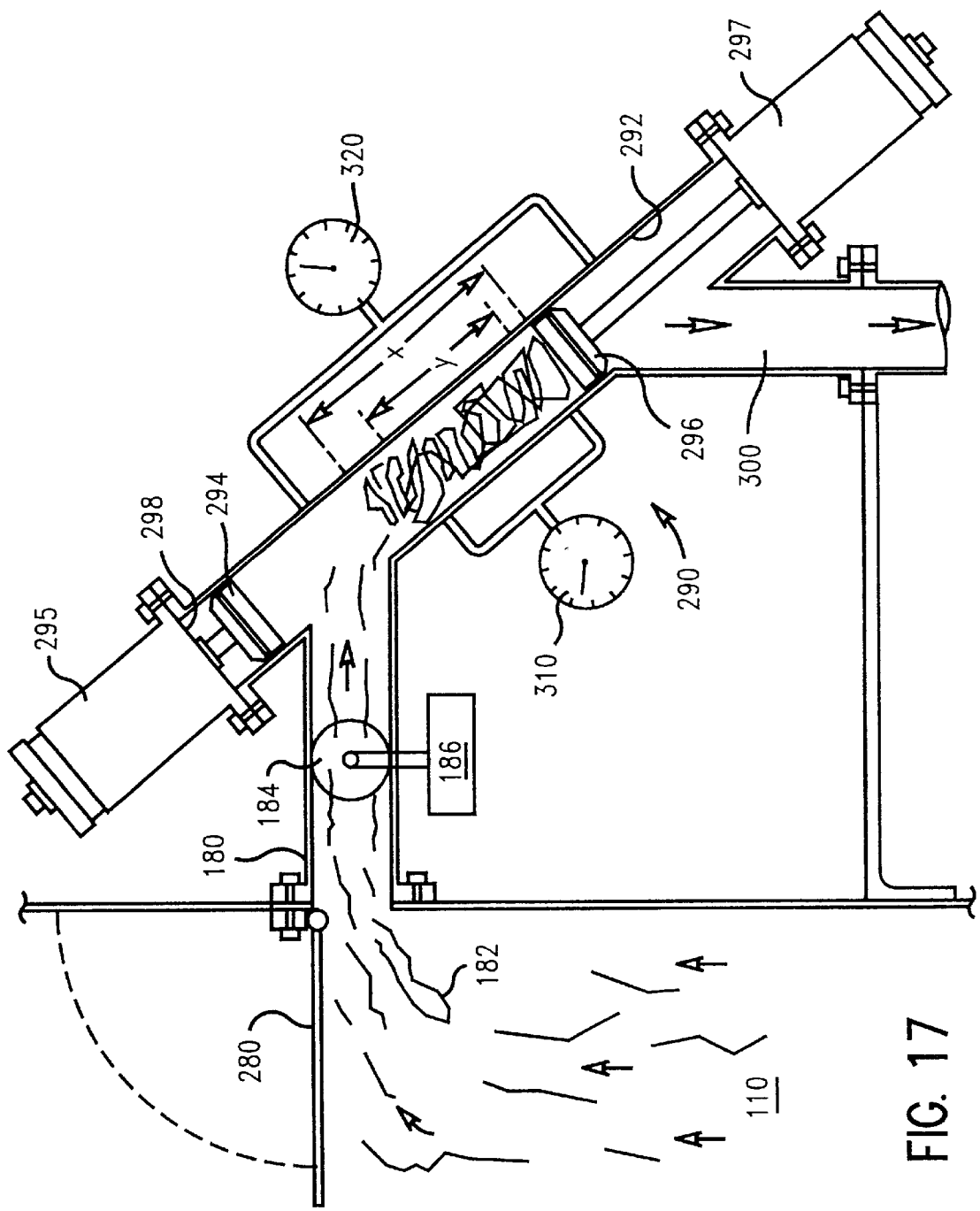
FIG. 17 is a mechanical schematic of the first embodiment of an in-situ sampling and micronaire testing apparatus for the present invention in the sample extraction mode.
Figure 18:
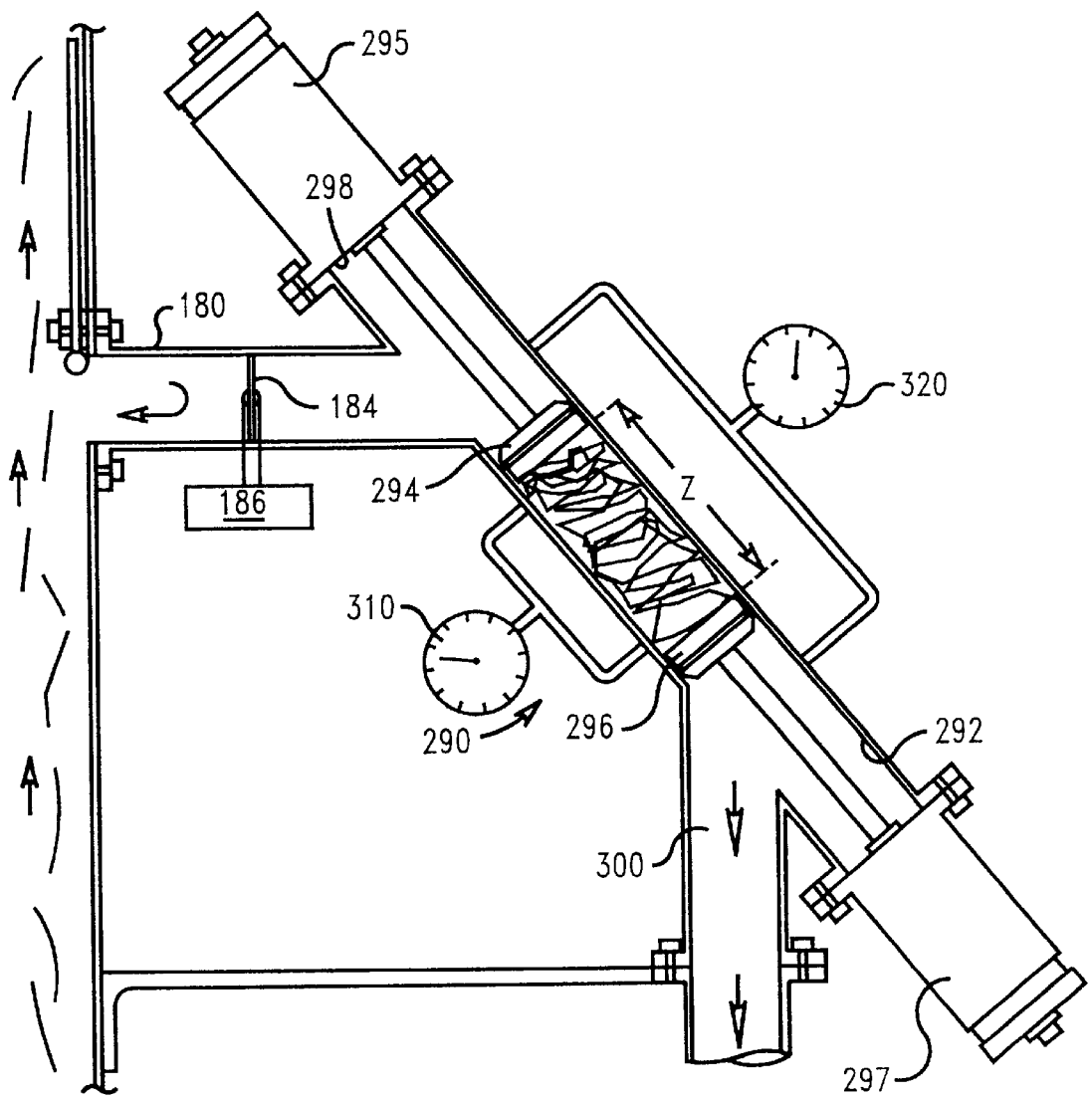
FIG. 18 is a mechanical schematic of the first embodiment in-situ sampling and micronaire testing apparatus in the air flow measurement mode.
Figure 19:
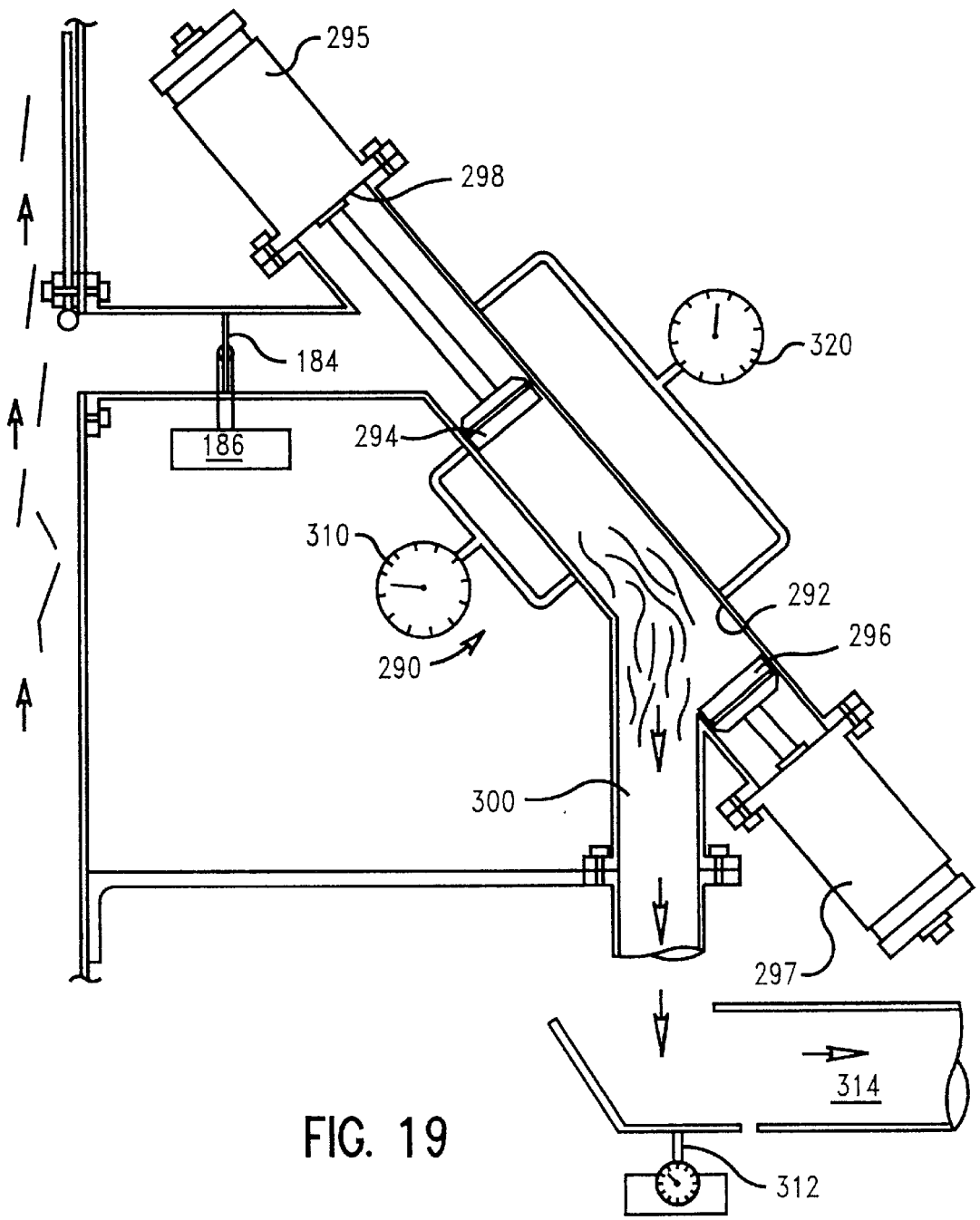
FIG. 19 is a mechanical schematic of the first embodiment in-situ sampling and micronaire testing apparatus in the sample discharge mode.

When:

$$RM = \left[\frac{(HMC - LMC)}{(LMP - HMP)}\right][LMC + (LMP - P)]$$

and:

$$X = 1 + [(W-10)100][0.00125 - |3.5 - RM|0.00015]$$

where, over a sample weight range of 8 to 12 grams:
M=Corrected micronaire value
RM=Raw micronaire value
HMC=High calibration cotton value
LMC=Low calibration cotton value
LMP=Pressure of low calibration cotton value HMP=Pressure of high calibration cotton value
P=Pressure of cotton under test
W=Weight of cotton under test, grams With respect to the example of FIG. 3, erection of the flapper element 130 provides a localized pressure region to complement an external draft drawn through the shunting duct 180 for extraction of a mainstream material sample into the micronaire testing apparatus. FIGS. 17 through 19 illustrate a sample extraction apparatus that exploits a perforated baffle 280 to establish a localized pressure zone around the opening 182 into the micronaire shunting duct 180. Like the flapper 130, the perforated baffle 280 is selectively rotated into and from an operative position within the duct 110 mainstream by a computer controlled rotary actuator not shown.

A first of our micronaire testing instruments comprises a cylinder bore 292 having pistons 294 and 296 to delineate the opposite axial ends of the piston bore 292. Each of the pistons 294 and 296 is reciprocable between an extended position and a retracted position relative to respective air pressure actuating cylinders 295 and 297. Either or both of the pistons 294 and 296 are perforated or porous for substantially free passage of air therethrough. However, such perforations are sufficiently small to block and retain any lint in an air flow stream passing therethrough. Between the rod-end face 298 of the cylinder 295 and the rod side of the piston 294 is an air flow rectification mechanism not shown that will permit an ingress of air flow into the cylinder bore 292 when the piston 294 is extended from the actuating cylinder 295. Such a mechanism may be an orifice through the wall of the cylinder bore 292 that is covered or otherwise closed by the piston 294 when in the retracted position.

In a presently preferred embodiment of this micronaire test apparatus, the micronaire cylinder bore diameter is about 1.5 inches. Axial length of a mid-length sample collection zone X of the cylinder bore 192 is about 6.0 inches. Between the face plane of the retracted piston 294 and the upstream delineation plane of the collection zone X, the sample shunting duct 180 penetrates the wall of the micronaire cylinder bore 292 at an intersection angle sufficiently small to allow a smooth transition of fluidized lint from the shunting duct 180 into the cylinder bore 292. Similarly, a vacuum draft duct 300 penetrates the wall of the cylinder bore 292 at a low angle of intersection between the downstream delineation plane of the sample collection zone X and the face of the retracted piston 296.

Figure 20:
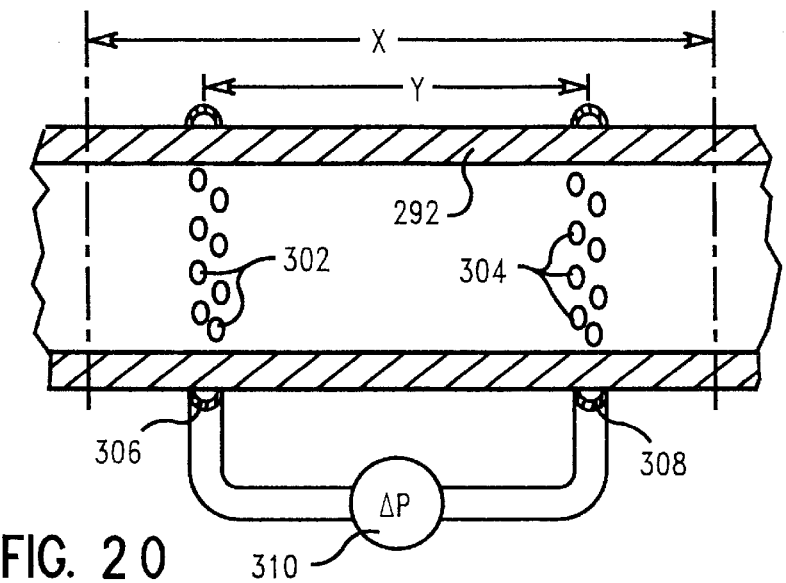
FIG. 20 is a sectioned enlargement of the air flow measuring section of the first embodiment micronaire test apparatus.

Within the sample collection zone X of the micronaire test bore 292 is a pressure differential measuring zone Y that is about 4.0 inches long. Referring to FIG. 20, the cylinder bore wall 292 is perforated about its circumference by two planar aligned aperture groups 302 and 304. The upstream group of apertures 302 open into an upstream manifold collar 306. The downstream group of apertures 304 open into a downstream manifold collar 308. The two manifold collars are operatively connected to a pressure differential signal transmitter 310.

An operational cycle of the micronaire test apparatus may begin with retraction of the upstream perforated piston 294 and extension of the downstream perforated piston 296 as illustrated by FIG. 17. Additionally, the valve disc 184 is turned by the rotary actuator 186 into planar alignment with the axis of shunting duct 180 to open the shunting duct into the sample collection zone X of micronaire cylinder bore 292. When a vacuum is drawn within the draft duct 300, an air flow through the perforated piston 296 draws fiber from the duct 110, through the shunting duct 180 and into the sample collection zone X. Entrained fiber is screened from this flow stream against the face of downstream piston 296 and accumulates within the sample collection zone X. As the accumulation grows and compresses, resistance to air flow through the accumulation increases accordingly. The quantity of accumulation is related to the pressure differential across the accumulated mass. When the pressure differential between the upstream apertures 302 and the downstream apertures 304, as monitored by the pressure differential transmitter 310, increases to a predetermined threshold level representative of a sufficient accumulation for a micronaire test, the control computer transmits a command signal to the rotary actuator 186 to close the disc valve 184. Sequentially, the upstream actuating cylinder 295 is activated to extend the upstream piston 294. At this point, both pistons 294 and 296 are fully extended to define a variable, albeit, determinable, volume Z within the cylinder bore 292. This volume Z is occupied by a substantially known quantity of compacted fiber.

It will be recalled that when the upstream piston 294 is fully retracted, exterior air passages into the cylinder bore 192 interior are closed. When the upstream piston 294 is extended, these exterior air passages are opened. Now, the air flow drawn by the vacuum draft duct 300 arrives from behind the upstream piston 294 and passes through the piston perforations into the accumulated fiber mass between the two piston faces. See FIG. 18. Since pressure loss through the pistons is either negligible or a calibrated value, air pressure loss through the compressed fiber mass along the axial length of volume Z is measured by the pressure differential transmitter 320. The control computer receives a signal from the transmitter 320 corresponding to the pressure differential value along the axial length of volume Z.

Referring to FIG. 19, after the second pressure differential is measured by transmitter 320, downstream piston 296 is retracted by the actuating cylinder 297 thereby opening the vacuum draft duct 300 directly into the cylinder bore 292. No longer restrained by the face of piston 296, the accumulated fiber mass moves as a plug into the draft duct 300. Duct 300 transports the plug to a weight scale 312. Signals corresponding to the fiber plug weight are transmitted to the control computer 200 for coordination with the signal value from the pressure differential transmitter 310 to resolve the micronaire value for this sample.

Figure 22:
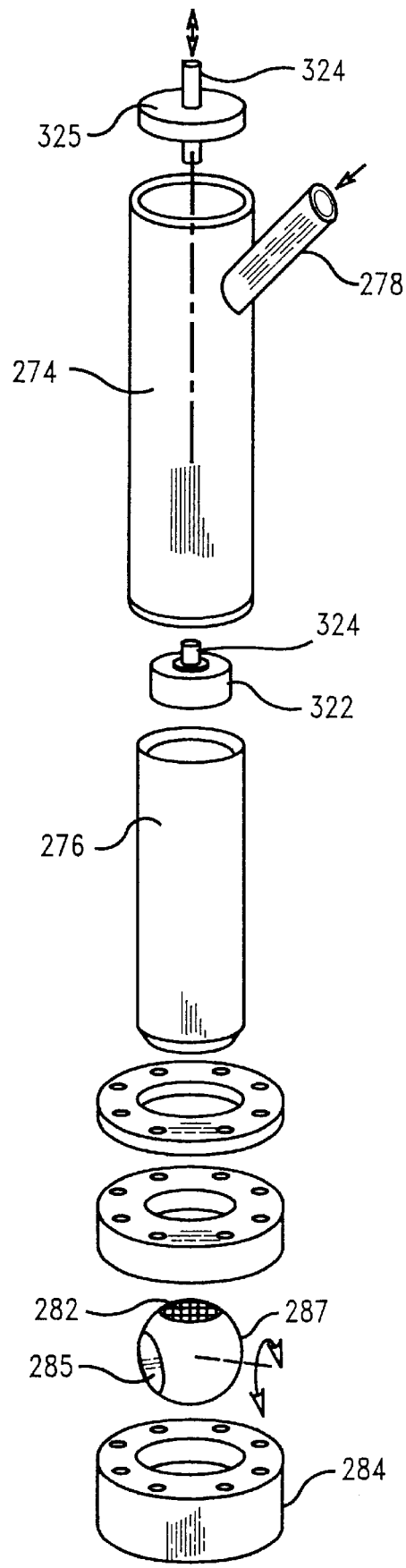
FIG. 22 is a first alternative micronaire testing apparatus.

Another embodiment of the micronaire test apparatus is shown by the exploded assembly illustration of FIG. 22. This arrangement requires only one fiber sample supply duct 278 that opens into a main tube body 274. An air draft flowing from the primary carrier duct (not depicted) passes along the main tube body 274, through the concentrically aligned measurement chamber 276 and through a pair of diametrically opposite, screened ports 282 of the flow control ball element 287. The ball element 287 also has an open port aperture 285. In a first rotary position controlled by a rotary actuator not shown, the screened ports 282 are open through the valve body 284. A second rotary position of the ball element 287, oriented 90° to the first, aligns the open port aperture 285 through the valve body 284.

A pressure differential measuring apparatus such as that described with respect to FIG. 20 is provided in the measurement chamber 276. Coaxially aligned with the measurement chamber 276 is a porous or perforated sample compression piston 322 secured to the end of a piston rod 324. The rod 324 shaft has a sliding penetration through the cap 325 for the main tube body 274. The exterior end of the compression piston rod 324 is secured to and positionally controlled by a position feedback air cylinder not shown. The position feed back air cylinder is mainly a double acting air cylinder having positive pressure driven displacement in either of opposite directions, selectively. In addition, however, the location of a displacement element such as a piston or rod is monitored relative to the cylinder or vice-versa. In either case, a position control signal is available to direct or report the relative location of a moving element such as the compression piston 322.

Cotton particles carried by the air draft from the primary transport duct are deposited against the screen of ball port 282. Accumulation of these particles within the measurement chamber 276 is detected and monitored by the pressure differential measuring apparatus of FIG. 20. When the predetermined pressure differential is detected corresponding to an adequate quantity of accumulated cotton sample, the control program terminates the air draft source and the entry of additional cotton into the measurement chamber. Next, the position feedback air cylinder advances the compression piston 322 into the measurement chamber 276 to a predetermined pressure load against the accumulated sample. Simultaneously, the piston position is reported to the control program thereby providing essential data for determination of the sample volume. At this state, a known air flow rate is induced through the compressed sample, passing through the compression piston 322 and the screened ball ports 282. Air flow resistance is determined from the pressure loss across the compressed cotton sample as function of the known flow rate. In turn, the micronaire value is calculated by the computer 200 as a function of the flow resistance and other known parameters.

With the airflow resistance concluded, the flow control ball element is rotated 90° to align the open port aperture 285. Further extension of the compression piston 322 by the position feedback air cylinder pushes the cotton sample out from the measurement chamber 276 and into an automated weight station 312 such as described with respect to the FIG. 19 embodiment. Such weight data may be referenced for mass verification. If desired, the extracted sample may also be discarded or recycled. In either case, upon discharge of the sample through the ball element 287, the ball element angular position is restored to the original sample, accumulation position.

Figure 23:
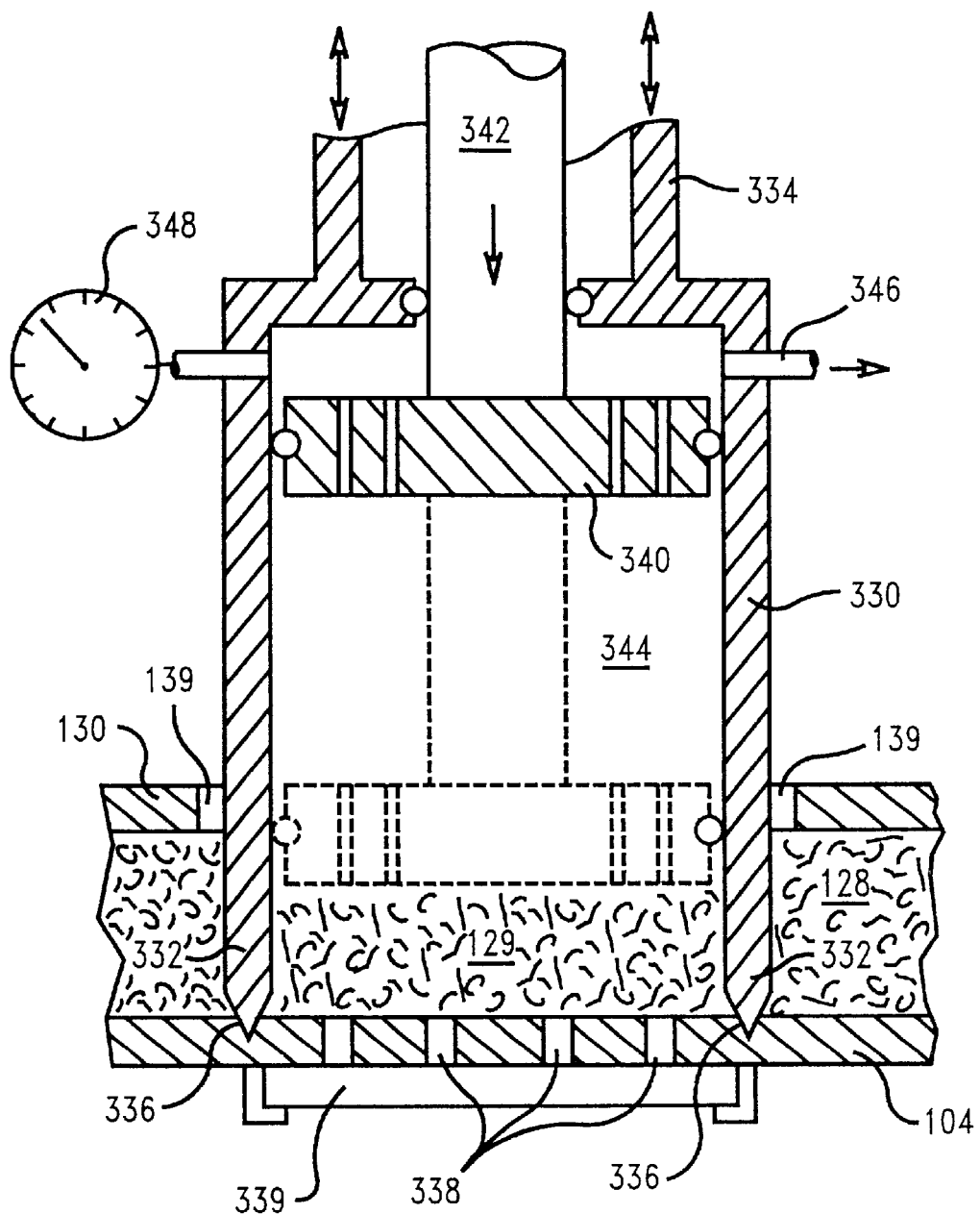
FIG. 23 is a second alternative micronaire testing apparatus.

A third micronaire testing embodiment of the invention comprises the device of FIG. 23 wherein a cotton sample core 129 is isolated from a larger accumulation 128 by a coring punch 330. The larger accumulation 128 may be consolidated by any of several known means such as a flapper 130 having a coring aperture 139. Aligned with the coring aperture 139 is the core punch 330 having an edged end 332. The punch body is reversibly translated by a hollow bore rod element 334 to selectively engage the edged end 332 with a circular sealing/cutting channel 336 in the duct wall 104. It is not essential that the core sample 129 be completely severed from the larger accumulation 128.

Within the perimeter circumscribed by the channel 336 are one or more duct wall apertures 338 that may be open to the atmosphere. A slide plate mechanism 339 may be positioned on the exterior side of the duct wall 104 to selectively close the apertures 338 if and when desired. Coaxially aligned within the measuring chamber 344 of the coring punch 330 is a perforated compression piston 340. The piston 340 is axially positioned by a rod 342 that is secured to the compression piston 340 and coaxially confined within the interior of rod 334. An air evacuation duct 346 penetrates the cylindrical wall of the coring punch body 330. Air pressure (or vacuum) within the measuring chamber 344 is sensed and transmitted to the control computer by pressure transducer 348.

This FIG. 23 embodiment of the micronaire invention is most useful in the overall process stream after the gin stand and lint cleaners where fully opened cotton samples may be obtained. Such fully opened samples are desired for assurance of uniform fiber density and sample consistency in the measuring chamber 344.

Actuation of the punch body rod 334 is a simple, full stroke movement that is coordinated with the compaction element 130. Positioning of the compression piston 340, however, is infinitely controlled between stroke limits within the measuring chamber 344 by a feedback controlled air or electric motor, not shown, that drives the piston rod 342. One function of the piston 340 feedback control is to regulate the piston 340 pressure (or force) on the sample 129 within a predetermined set-point range. Secondly, the feedback control reports the piston 340 face position for determination of a corresponding measuring chamber volume of infinite variability between the extreme limits of the piston 340 stroke.

With a sample 129 under the predetermined load of the compression piston 340 while occupying a known volume within the measuring chamber, the corresponding sample 129 weight is determined by algorithm. A known air flow rate drawn through the duct 346 is coordinated with the corresponding chamber pressure measured by the transducer 348. From this data array, a "weightless" micronaire value may be calculated.

As a further application of the FIG. 23 embodiment, cotton sample properties corresponding to prior at "maturity" values may be determined. According to the prior art "maturity value" measurement procedure, a known weight quantity of fully open cotton is compressed to a first predetermined volume, a known "low" air flow rate is drawn through the first compressed volume and the pressure differential noted. Subsequently, the same sample is further compressed to a second predetermined volume and a known "high" air flow rate is drawn through the second volume. The pressure differential of the "high" air flow volume is combined with that of the "low" air flow pressure differential value to calculate the fiber maturity value using a classical ASTM formula.

A modified maturity value may be determined from an operational procedure using the FIG. 23 embodiment in which the compression piston 340 is programmed to two or more positions, progressively. At each of the preprogrammed piston positions definitive of a corresponding volume, the air flow rate through the sample, the pressure differential from the sample and the piston load are noted data. From the noted data, the cotton maturity value may be determined. This maturity value determination process may be incremental or continuous.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments were chosen and described to provide the best illustrations of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally and equitably entitled.

What is claimed is:

1. A system for controlling the processing of fiber through a fiber processing plant, the plant having a plurality of auxiliary treatment units and ducting for fluidized transport of a fiber flow stream to, through and around said treatment units, said system comprising:

measuring means for measuring a plurality of physical properties of fiber in said flow stream including fiber strength and for translating values representing the physical property measured to corresponding sensor data;

processing means coupled to said measuring means, said processing means processing said sensor data for selecting an optimum combination of said plurality of auxiliary treatment units to process said fiber flow stream, based at least in part on the sensor data corresponding to fiber strength; and flow stream control means in said ducting respective to at least one of said auxiliary treatment units, operation of said flow stream control means being responsive to said processing means wherein said processing means activates said flow stream control means to divert said fiber flow stream into or from the respective auxiliary treatment unit based upon the optimum combination.

2. A system for controlling the processing of fiber through a fiber processing plant, the plant having a plurality of auxiliary treatment units and ducting for fluidized transport of a fiber flow stream to, through and around said treatment units, said system comprising:

measuring means for measuring a plurality of physical properties of fiber in said flow stream including fiber length and for translating values representing the physical property measured to corresponding sensor data;

processing means coupled to said measuring means, said processing means processing said sensor data for selecting an optimum combination of said plurality of auxiliary treatment units to process said fiber flow stream, based at least in part on the sensor data corresponding to fiber length; and flow stream control means in said ducting respective to at least one of said auxiliary treatment units, operation of said flow stream control means being responsive to said processing means wherein said processing means activates said flow stream control means to divert said fiber flow stream into or from the respective auxiliary treatment unit based upon the optimum combination.

3. A system as described by claims 1 or 2 wherein said measuring means also measures fiber elongation.

4. A system as described by claim 1 or 2 wherein said measuring means also measure fiber length variation.

5. A system as described by claim 1 or 2 wherein said measuring means also measures micronaire.

6. A fiber quality conditioning system comprising:

a plurality of fiber processing stations, each having respective capacities to modify a physical characteristic of fiber;

a fluidized transport system for transfer of a fluidized fiber flow stream through, between and from said processing stations, said transport system including flow stream carrier ducting;

fluidized flow control means for regulating alternative fiber flow paths within said transport system;

sample gathering means secured to said carrier ducting for consolidating and concentrating a sample quantity of fiber from a fluidized flow stream of fiber within said carrier ducting, said sample gathering means also being operative to present a concentrated fiber sample to sensing means for measuring a plurality of physical characteristics of said fiber sample including a fiber strength characteristic;

signal generation means responsive to physical characteristics measured by said sensing means for generating signals proportional to values respective to corresponding physical characteristics including the fiber strength characteristic;

process control means responsive to the signals of said signal generation means for activating said flow control means to direct fiber flow through a predetermined sequence of conditioning stations for modification of the physical characteristics of fiber in said flow stream based at least in part on the fiber strength characteristic.

7. A fiber quality conditioning system comprising:

a plurality of fiber processing stations, each having respective capacities to modify a physical characteristic of fiber;

a fluidized transport system for transfer of a fluidized fiber flow stream through, between and from said processing stations, said transport system including flow stream carrier ducting;

fluidized flow control means for regulating alternative fiber flow paths within said transport system;

sample gathering means secured to said carrier ducting for consolidating and concentrating a sample quantity of fiber from a fluidized flow stream of fiber within said carrier ducting, said sample gathering means also being operative to present a concentrated fiber sample to sensing means for measuring a plurality of physical characteristics of said fiber sample including a fiber length characteristic;

signal generation means responsive to physical characteristics measured by said sensing means for generating signals proportional to values respective to corresponding physical characteristics including the fiber length characteristic;

process control means responsive to the signals of said signal generation means for activating said flow control means to direct cotton flow through a predetermined sequence of conditioning stations for modification of the physical characteristics of fiber in said flow stream based at least in part on the fiber length characteristic.

8. A fiber quality conditioning system as described by claim 6 or 7 wherein said sensing means also measures cotton color and moisture content.

9. A fiber quality conditioning system as described by claim 6 or 7 wherein said sensing means also measures micronaire.

10. A fiber quality conditioning system as described by claim 6 or 7 wherein said sensing means also measures cotton fiber length.

11. A fiber quality conditioning system as described by claim 6 or 7 wherein said sensing means also measure trash content.

12. A fiber quality conditioning system as described by claim 6 or 7 wherein said sensing means also measure micronaire.

13. A fiber processing system having a fluidized transport system for transfer of a fiber/entrained air flow through said processing system, the improvement comprising:

means for extracting a test sample of fiber from a fiber entrained air flow within said transport system;

means for depositing said test sample of fiber in a test chamber; and, means for determining the micronaire value of said sample.

14. In combination with a seed cotton drying facility, the improvement comprising:

first means to extract a first test sample flow from a cotton supply stream into said drying facility, second means to extract a second test sample flow from a cotton discharge stream from said drying facility, third means for measuring the average fiber length in said first sample flow;

fourth means for measuring the average fiber length in said second sample flow; and, fifth means for measuring the average fiber length differential between measurements of the third and fourth means.

15. In combination with a cotton gin having a fluidized transport system for delivery of an air entrained seed cotton flow stream to said gin and an air entrained lint cotton flow stream from said gin, the improvement comprising:

first means to extract a first test sample flow stream from said seed cotton flow stream;

second means to extract a second test sample flow stream from said lint cotton flow stream;

third means for measuring the fiber length in said first sample flow stream;

fourth means for measuring the fiber length in said second sample flow stream; and, fifth means for measuring the fiber length differential between measurements of said third and fourth means.

16. In combination with a cotton gin having a fluidized transport system for delivery of an air entrained seed cotton flow stream to said gin and an air entrained lint cotton flow stream from said gin, the improvement comprising:

first means to extract a first test sample flow stream from said seed cotton flow stream;

second means to extract a second test sample flow stream from said lint cotton flow stream;

third means for measuring the fiber strength in said first sample flow stream;

fourth means for measuring the fiber strength in said second sample flow stream; and, fifth means for measuring the fiber strength differential between measurements of said third and fourth means.

17. In combination with a cotton gin having a fluidized transport system for delivery of an air entrained seed cotton flow stream to said gin and an air entrained lint cotton flow stream from said gin, the improvement comprising:

first means to extract a first test sample flow stream from said seed cotton flow stream;

second means to extract a second test sample flow stream from said lint cotton flow stream;

third means for measuring the fiber micronaire in said first sample flow stream;

fourth means for measuring the fiber micronaire in said second sample flow stream; and, fifth means for measuring the fiber micronaire differential between measurements of said third and fourth means.

18. A system for controlling the processing of fiber through a fiber processing plant, the plant having a plurality of auxiliary treatment units and ducting for fluidized transport of a fiber flow stream to, through and around said treatment units, said system comprising:

measuring means for measuring a plurality of physical properties of fiber in said flow stream including fiber micronaire and for translating values representing the physical property measured to corresponding sensor data;

processing means coupled to said measuring means, said processing means processing said sensor data for selecting an optimum combination of said plurality of auxiliary treatment units to process said fiber flow stream based at least in part on the sensor data corresponding to fiber micronaire; and flow stream control means in said ducting respective to at least one of said auxiliary treatment units, operation of said flow stream control means being responsive to said processing means wherein said processing means activates said flow stream control means to divert said fiber flow stream into or from the respective auxiliary treatment unit based upon the optimum combination.

19. A fiber quality conditioning system comprising:

a plurality of fiber processing stations, each having respective capacities to modify a physical characteristic of fiber;

a fluidized transport system for transfer of a fluidized fiber flow stream through, between and from said processing stations, said transport system including flow stream carrier ducting;

fluidized flow control means for regulating alternative fiber flow paths within said transport system;

sample gathering means secured to said carrier ducting for consolidating and concentrating a sample quantity of fiber from a fluidized flow stream of fiber within said carrier ducting, said sample gathering means also being operative to present a concentrated fiber sample to sensing means for measuring a plurality of physical characteristics of said fiber sample including a fiber micronaire characteristic;

signal generation means responsive to physical characteristics measured by said sensing means for generating signals proportional to values respective to corresponding physical characteristics including the fiber micronaire characteristic;

process control means responsive to the signals of said signal generation means for activating said flow control means to direct fiber flow through a predetermined sequence of conditioning stations for modification of the physical characteristics of fiber in said flow stream based at least in part on the fiber micronaire characteristic.

* * * * *

UNITED STATES PATENT AND TRADEMARK OFFICE
CERTIFICATE OF CORRECTION

Patent No : 6,112,131

Dated : August 29, 2000

Inventor(s) : Ghorashi et al.

It is certified that error appears in the above-identified patent and that said Letters Patent are hereby corrected as shown below:

Column 18, line 51, after "volume", insert a new line 52 comprising:

$$--M=(RM)^x--$$

Signed and Sealed this

Twenty-ninth Day of May, 2001

*Attest:*

NICHOLAS P. GODICI

*Attesting Officer*     *Acting Director of the United States Patent and Trademark Office*